(12) United States Patent
Wada et al.

(10) Patent No.: US 9,730,968 B2
(45) Date of Patent: Aug. 15, 2017

(54) THERAPEUTIC AGENT FOR ISCHEMIC DISEASES

(71) Applicant: Anaeropharma Science, Inc., Tokyo (JP)

(72) Inventors: Yuko Wada, Nagano (JP); Yuko Shimatani-Shibata, Nagano (JP); Hitomi Shimizu-Matsuhashi, Nagano (JP); Takayuki Sasaki, Tokyo (JP); Hiromi Yonekura, Tokyo (JP)

(73) Assignee: Anaeropharma Science, Inc., Tokyo (JP)

( * ) Notice: Subject to any disclaimer, the term of this patent is extended or adjusted under 35 U.S.C. 154(b) by 0 days.

(21) Appl. No.: 14/690,528

(22) Filed: Apr. 20, 2015

(65) Prior Publication Data

US 2015/0290259 A1 Oct. 15, 2015

Related U.S. Application Data

(60) Continuation-in-part of application No. 13/548,544, filed on Jul. 13, 2012, now abandoned, and a continuation-in-part of application No. 13/015,806, filed on Jan. 28, 2011, now Pat. No. 8,535,939, application No. 14/690,528, which is a continuation-in-part of application No. 13/749,428, filed on Jan. 24, 2013, now abandoned, which is a division of application No. 12/425,001, filed on Apr. 16, 2009, now Pat. No. 8,383,398.

(60) Provisional application No. 61/507,590, filed on Jul. 13, 2011, provisional application No. 61/299,922, filed on Jan. 29, 2010, provisional application No. 61/124,528, filed on Apr. 17, 2008.

(51) Int. Cl.
| | |
|---|---|
| *A61K 35/745* | (2015.01) |
| *A61K 38/18* | (2006.01) |
| *C12N 15/74* | (2006.01) |
| *C07K 14/50* | (2006.01) |
| *A61K 35/00* | (2006.01) |
| *A61K 48/00* | (2006.01) |

(52) U.S. Cl.
CPC ........ *A61K 35/745* (2013.01); *A61K 38/1825* (2013.01); *C12N 15/746* (2013.01); *A61K 48/00* (2013.01); *A61K 2035/11* (2013.01); *C07K 14/503* (2013.01)

(58) Field of Classification Search
None
See application file for complete search history.

(56) References Cited

U.S. PATENT DOCUMENTS

| | | | |
|---|---|---|---|
| 6,416,754 B1 | 7/2002 | Brown et al. | |
| 6,652,849 B2 | 11/2003 | Brown et al. | |
| 8,383,398 B2 | 2/2013 | Shimatani-Shibata et al. | |
| 8,535,939 B2 | 9/2013 | Shimatani-Shibata et al. | |
| 9,228,191 B2 | 1/2016 | Shimatani-Shibata et al. | |
| 2003/0103952 A1 | 6/2003 | Brown et al. | |
| 2003/0161788 A1 | 8/2003 | Zhao et al. | |
| 2004/0014221 A1 | 1/2004 | Ji et al. | |
| 2005/0025745 A1 | 2/2005 | Fujimori et al. | |
| 2005/0227910 A1 | 10/2005 | Yang et al. | |
| 2008/0112928 A1 | 5/2008 | Loessner et al. | |
| 2009/0123426 A1 | 5/2009 | Li et al. | |
| 2009/0176747 A1 | 7/2009 | Pommier et al. | |
| 2009/0264513 A1 | 10/2009 | Shimatani-Shibata et al. | |
| 2009/0291469 A1 | 11/2009 | David | |
| 2011/0189757 A1 | 8/2011 | Shimatani-Shibata et al. | |
| 2011/0189758 A1 | 8/2011 | Shimatani-Shibata et al. | |
| 2011/0190472 A1 | 8/2011 | Shimatani-Shibata et al. | |
| 2013/0095072 A1 | 4/2013 | Wada et al. | |
| 2013/0122582 A1 | 5/2013 | Shimatani-Shibata et al. | |

FOREIGN PATENT DOCUMENTS

| | | |
|---|---|---|
| EP | 1 227 152 A1 | 7/2002 |
| JP | 2002/97144 A | 4/2002 |
| JP | 2008-092956 | 4/2008 |
| JP | 2008-519002 | 6/2008 |
| WO | WO 02/074798 A2 | 9/2002 |
| WO | WO 2006/57289 | 6/2006 |
| WO | WO 2007/136107 | 11/2007 |
| WO | WO 2008/091375 | 7/2008 |
| WO | WO 2009/128272 | 10/2009 |
| WO | WO 2010/126073 | 11/2010 |

OTHER PUBLICATIONS

Genbank Submission; NCBI; Accession No. AB187597.1; Mar. 5, 2005. Tanaka et al.
Xu et al., A new expression plasmid in Bifidobacterium longum as a delivery system of endostatin for cancer gene therapy. Cancer Gene Ther. Feb. 2007;14(2):151-7. Epub Oct. 27, 2006.
Genbank submission; Accession No. CBK70834.1; Jul. 13, 2010. Pajon et al.
Genbank submission; Accession No. ACD98321.1; Dec. 15, 2009. Lee et al.
Argnani et al., A convenient and reproducible method to genetically transform bacteria of the genus *Bifidobacterium*. Microbiology. Jan. 1996;142 ( Pt 1):109-14.

(Continued)

*Primary Examiner* — Antonio Galisteo Gonzalez
(74) *Attorney, Agent, or Firm* — Wolf, Greenfield & Sacks, P.C.

(57) ABSTRACT

[Object]
To provide a gene transfer carrier that specifically accumulates only at a disease site even with systemic administration, has a high protein expression rate, and disappears from the disease site accompanying a cure, and a method for the treatment of an ischemic disease using same.
[Solution means]
The above-mentioned object has been accomplished by providing a gene transfer carrier formed from an anaerobic bacterium that can grow specifically at the site of an ischemic disease and can express at least one type of protein that is useful for the diagnosis or treatment of an ischemic disease, a pharmaceutical composition containing the gene transfer carrier, and a treatment method for an ischemic disease utilizing same.

19 Claims, 19 Drawing Sheets

(56) References Cited

OTHER PUBLICATIONS

Bork, Powers and pitfalls in sequence analysis: the 70% hurdle. Genome Res. Apr. 2000;10(4):398-400.

Bowie et al., Deciphering the message in protein sequences: tolerance to amino acid substitutions. Science. Mar. 16, 1990;247(4948):1306-10.

Corneau et al., Molecular characterization of three plasmids from Bifidobacterium longum Plasmid. Mar. 2004;51(2):87-100.

Cronin et al., Progress in genomics, metabolism and biotechnology of bifidobacteria. Int J Food Microbiol. Sep. 1, 2011;149(1):4-18. doi: 10.1016/j.ijfoodmicro.2011.01.019. Epub Jan. 26, 2011.

Deng et al., Signal peptide of Arabinosidase enhances secretion of interferon-alpha2b protein by Bifidobacteria longum. Arch Microbiol. Sep. 2009;191(9):681-6. doi: 10.1007/s00203-009-0496-5 Epub Aug. 4, 2009.

Fujimori et al., "The genus *Bifidobacterium* for cancer gene therapy," 2002, Curr. Opin. Drug. Discov. Devel., 5:200-203.

Gupta et al., "Human Studies of Angiogenic Gene Therapy," Circ. Res. 2009, vol. 105: 724-736.

Hedman et al., Safety and feasibility of catheter-based local intracoronary vascular endothelial growth factor gene transfer in the prevention of postangioplasty and in-stent restenosis and in the treatment of chronic myocardial ischemia: phase II results of the Kuopio Angiogenesis Trial (KAT). Circulation. Jun. 3, 2003;107(21):2677-83. Epub May 12, 2003.

Kohno et al., Expression of EHEC verotoxin 1B subunit fused to secreted signal peptides of S. bovis alpha-amylase in Bifidobacterium longum. Journal of Japanese Biochemical Society Shoroku CD, 4P-1217 (2007). Japanese.

Lee et al., "Comparative genomic analysis of the gut bacterium Bifidobacterium longum reveals loci susceptible to deletion during pure culture growth," BMC Genomics 2008, vol. 9: 247, 1-16.

MacConaill et al., "Investigation of Protein Export in Bifidobacterium breve UCC2003," Appl Environ Microbiol, 2003, vol. 69, No. 12: 6994-7001.

Moon et al., Secretion of recombinant pediocin PA-1 by Bifidobacterium longum, using the signal sequence for bifidobacterial alpha-amylase. Appl Environ Microbiol. Sep. 2005;71(9):5630-2.

Morishita et al., "Phase Ulla Clinical Trial of Therapeutic Angiogenesis Using Hepatocyte Growth Factor Gene Transfer to Treat Critical Limb Ischemia," Arterioscler Thromb Vasc Biol 2011, vol. 31: 713-720.

Nakamura et al., "Cloned cytosine deaminase gene expression of Bifidobacterium longum and application to enzyme/pro-drug therapy of hypoxic solid tumors," 2002, Biosci. Biotechnol. Biochem., 66:2362-2366.

Park et al., Heterologous gene expression and secretion in Bifidobacterium longum. Lait. 2005;85:1-8.

Posno et al., Incompatibility of Lactobacillus Vectors with Replicons Derived from Small Cryptic Lactobacillus Plasmids and Segregational Instability of the Introduced Vectors. Appl Environ Microbiol. Jun. 1991;57(6):1822-1828.

Reyes Escodigo et al., A novel binary expression vector for production of human IL-10 in *Escherichia coli* and Bifidobacterium longum. Biotechnol Lett. Aug. 2007;29(8):1249-53. Epub May 9, 2007.

Rhim, S. L. et al., "Expression and secretion of Bifidobacterium adolescentis amylase by Bifidobacterium longum," Biotechnology Letters 2006; 28:163-168.

Rossi et al., An efficient transformation system for *Bifidobacterium* spp. Letters in Applied Microbiology 1997;24:33-36.

Sánchez et al., A preliminary analysis of Bifidobacterium longum exported proteins by two-dimensional electrophoresis. J Mol Microbiol Biotechnol. 2008;14(1-3):74-9.

Schell et al., "The genome sequence of Bifidobacterium longum reflects its adaptation to the human gastrointestinal tract," Proc Natl Acad Sci USA, 2002, vol. 99., No. 22: 14422-14427.

Sela et al., The genome sequence of *Bifidobacterium longum* subsp. infantis reveals adaptations for milk utilization within the infant microbiome. Proc Natl Acad Sci U S A. Dec. 2, 2008;105(48):18964-9. doi: 10.1073/pnas.0809584105. Epub Nov. 24, 2008.

Shareck et al., Cloning vectors based on cryptic plasmids isolated from lactic acid bacteria: their characteristics and potential applications in biotechnology. Crit Rev Biotechnol. 2004;24(4):155-208.

Shimizu-Kadota et al., Shuttle plasmid vectors for Lactobacillus casei and *Escherichia coli* with a minus origin. Appl Environ Microbiol. Nov. 1991;57(11):3292-300.

Shkoporov, A. N. et al., "Production of human basic fibroblast growth factor (FGF-2) in Bifidobacterium breve using a series of novel expression/secretion vectors," Biotechnology Letters 2008; 30:1983-1988.

Shoemaker et al., Conjugal transfer of a shuttle vector from the human colonic anaerobe Bacteroides uniformis to the ruminal anaerobe Prevotella (Bacteroides) ruminicola B(1)4. Appl Environ Microbiol. Aug. 1991;57(8):2114-20.

Tanaka et al., "Structural and functional analysis of pTB6 from Bifidobacterium longum," 2005, Biosci, Biotechnol. Biochem., 69:422-425.

Waterfield et al., An origin of DNA replication from Lactococcus lactis bacteriophage c2. Appl Environ Microbiol. Apr. 1996;62(4):1452-3.

Yazawa et al., "Bifidobacterium longum as a delivery system for gene therapy of chemically induced rat mammary tumors," 2001, Breast Cancer Res. Treat., 66:165-170.

Yazawa et al., "Bifidobacterium longurn as a delivery system for cancer gene therapy: selective localization and growth in hypoxic tumors," 2000, Cancer Gene Ther. 7:269-274.

ADMINISTRATION OF *B. longum* DID NOT AFFECT
THE ISCHEMIC STATE OF THE LOWER LIMB.

GRAM STAINING
(4TH DAY AFTER *B. longum* WAS SYSTEMICALLY ADMINISTERED)

ISCHEMIC LIMB (x400)

NON-ISCHEMIC LIMB (x400)

ISCHEMIC LIMB (x1000)

ISCHEMIC MODEL 168 H AFTER SYSTEMIC ADMINISTRATION

NORMAL
HEART MUSCLE (x400)   INFARCTION SITE (x400)

NORMAL
HEART MUSCLE (x400)   INFARCTION SITE (x400)

pFGF12a: *B. longum* 105A/pFGF12a
NC: *B. longum* 105A/pBEshuttle
PC: recombinant hFGF2 standard pFGF12a: *B. breve* JCM1192/pFGF12a
NC: *B. breve* JCM1192/pBEshuttle
PC: recombinant hFGF2 standard

SEQUENCE LISTING

<160> NUMBER OF SEQ ID NOS: 40

<210> SEQ ID NO 1
<211> LENGTH: 141
<212> TYPE: DNA
<213> ORGANISM: Artificial
<220> FEATURE:
<223> OTHER INFORMATION: DNA sequence of signal peptide SP1

<400> SEQUENCE: 1

```
atggcggaaa ctaccgttaa gcccacgaag cttgctgtta ttggtgccgg tgccgttggc      60
tccaccctcg ccttcgccgc tgcccagcgt ggcatcgctc gcgagatcgt gcttgaagac     120
atcgccaagg agcgcgtgga a                                               141
```

```
<210> SEQ ID NO 2
<211> LENGTH: 156
<212> TYPE: DNA
<213> ORGANISM: Artificial
<220> FEATURE:
<223> OTHER INFORMATION: DNA sequence of signal peptide SP2

<400> SEQUENCE: 2
gtgggtatga ctgagaacgc cgtaaatact gccgtgactt ccacctcctc tcccgcaatt      60
cccgccgaga cttccgccgt ctcccccgca actcgcgcag ccaaccgccc gctgggcaca     120
ccgctgggca agcaccccac ccgcgtgctg tttttg                               156

<210> SEQ ID NO 3
<211> LENGTH: 165
<212> TYPE: DNA
<213> ORGANISM: Artificial
<220> FEATURE:
<223> OTHER INFORMATION: DNA sequence of signal peptide SP3

<400> SEQUENCE: 3
atgttcaata agcgacacat cgtccgtacc attgcggcca ccgccagcat cctggctctg      60
tcgttcaccg cagcctgcgg ttccggccag tccaccgcat ccaattccac cgattcggac     120
gacatcaccc agcagacgta caagccgggc aagctgacca tcgcc                     165

<210> SEQ ID NO 4
<211> LENGTH: 195
<212> TYPE: DNA
<213> ORGANISM: Artificial
<220> FEATURE:
<223> OTHER INFORMATION: DNA sequence of signal peptide SP4

<400> SEQUENCE: 4
atgaccactc acaacagcca gtattccgcc gaaaccgccc atcccgacaa gcaggaaagc      60
agcccggcgc cgaccgccgc cggcaccacg gccagtaacg tctccacaac tggcaacgca     120
accacgccgg acgccagcat cgccctcaac gccgacgcca ctccggtagc cgacgttccc     180
ccgcgtctgt tcggc                                                      195

<210> SEQ ID NO 5
<211> LENGTH: 177
<212> TYPE: DNA
<213> ORGANISM: Artificial
<220> FEATURE:
<223> OTHER INFORMATION: DNA sequence of signal peptide SP5

<400> SEQUENCE: 5
atgaccgcga ttgacgagac cgaccagcgc atcctcacca tgctggaggc cgacggccgc      60
gccacgctcg cgcaactggc ccaggcgacc ggactgtccg tctccgccgc ccagtcgcgc     120
gtgcagaagc tggagaagcg cggcatcatc aagggataca aggccatcat cgaccaa       177

<210> SEQ ID NO 6
<211> LENGTH: 141
<212> TYPE: DNA
<213> ORGANISM: Artificial
<220> FEATURE:
<223> OTHER INFORMATION: DNA sequence of signal peptide SP6

<400> SEQUENCE: 6
atgaagattg cggttgcagg gactggctac gttggattgt ctgtcgcttt gctgctcgct      60
cagcacaatg aagttcatgc actcgacatc attcccgaga aagtcgagca gttaaacaat     120
```

-continued

```
gggaaaagtc ctattgtcga t                                         141

<210> SEQ ID NO 7
<211> LENGTH: 126
<212> TYPE: DNA
<213> ORGANISM: Artificial
<220> FEATURE:
<223> OTHER INFORMATION: DNA sequence of signal peptide SP7

<400> SEQUENCE: 7
atgtttgcgt gcgtagcccc gtttgcctct gccgattccg cgcagacgag tgctgtggtg    60
tcctcacgtt ctttcccgaa ggcgagttcg gtgaagaaga atttgttcgc cgaatccacc   120
tccacc                                                              126

<210> SEQ ID NO 8
<211> LENGTH: 204
<212> TYPE: DNA
<213> ORGANISM: Artificial
<220> FEATURE:
<223> OTHER INFORMATION: DNA sequence of signal peptide SP8

<400> SEQUENCE: 8
atggttggtg acgacaccgt gacgatatgg tcgattgacg aatcccgaca gccgattcgc    60
cgcgttcgtc tgagtcgatt ccccgctggg gcgcgaatat gccttatcat gggttgcatg   120
acacccgcag agcgtgcgag cgcagtcgca tttgcactca agaactgcgc actggaagcg   180
atgacgccgg gcgaggcaac gatg                                          204

<210> SEQ ID NO 9
<211> LENGTH: 126
<212> TYPE: DNA
<213> ORGANISM: Artificial
<220> FEATURE:
<223> OTHER INFORMATION: DNA sequence of signal peptide SP9

<400> SEQUENCE: 9
atgggcacca tgatgcgaat aggactgacc ggcggcatcg ccgcgggcaa aagtacggtg    60
gcggcgcaac tcaagcaact cggcgcgttg catatcgact acgatgcgct ggcgcatcag   120
atcgtc                                                              126

<210> SEQ ID NO 10
<211> LENGTH: 153
<212> TYPE: DNA
<213> ORGANISM: Artificial
<220> FEATURE:
<223> OTHER INFORMATION: DNA sequence of signal peptide SP10

<400> SEQUENCE: 10
atgatgactg gtgcacaggc cgctcactgt ggttctgtat ccgcaatttc gctgggactg    60
cccgtttcca cggcgattcc cgaagccaaa ggctcactgc cgaaagcctt gttcgtaggc   120
aaagcgccga tttccggcaa actcaagcag cga                                153

<210> SEQ ID NO 11
<211> LENGTH: 156
<212> TYPE: DNA
<213> ORGANISM: Artificial
<220> FEATURE:
<223> OTHER INFORMATION: DNA sequence of signal peptide SP11

<400> SEQUENCE: 11
atgaagttca ccgttgctaa gaaggccatt gcacttaccg gtgcggttgc catgctgggt    60
```

```
tccgttgccg cctgcggttc cgacaccgcc agtggcaagc cggctcaaga taaggacgtt      120
accgaaatca ccgtgtgggc ttgggagccc acgctg                                156

<210> SEQ ID NO 12
<211> LENGTH: 171
<212> TYPE: DNA
<213> ORGANISM: Artificial
<220> FEATURE:
<223> OTHER INFORMATION: DNA sequence of signal peptide SP12

<400> SEQUENCE: 12
atggtgtctt tcaataaact gacccgtact cttgctggca tcgctgccgc cgcgttgatc      60
gttccgctgg ccgcctgtgg tggctccggc aatggtggca ctgccaccgc cgaaggtatc     120
ccggccaagg gcaccgacga tggtaccgag atcaccctgt ggacccgttc c              171

<210> SEQ ID NO 13
<211> LENGTH: 138
<212> TYPE: DNA
<213> ORGANISM: Artificial
<220> FEATURE:
<223> OTHER INFORMATION: DNA sequence of signal peptide SP13

<400> SEQUENCE: 13
atggtcgccg tcctcaggtt cggctgtctg ccatcatgct cggtcttgac tcattattta      60
tccgtgcatg ctgtaggcaa tcggcctgtg gtcggtctcc tcccgcaact tatattgctg     120
tgctgtgcta gcgagtct                                                   138

<210> SEQ ID NO 14
<211> LENGTH: 186
<212> TYPE: DNA
<213> ORGANISM: Artificial
<220> FEATURE:
<223> OTHER INFORMATION: DNA sequence of signal peptide SP14

<400> SEQUENCE: 14
ttgccgggac ctatatgtcc ccggcaacaa cagccgtata tacgctaccg atcagtgctg      60
ccctcatcat ccttggcacc tgccgtggcg gcctcagtct ccttggcgtt ccacccggcg     120
acggcattcc aaccactcca tccgatgacc actagcaagc acagcgagaa gacaatagtg     180
gcccaa                                                                186

<210> SEQ ID NO 15
<211> LENGTH: 150
<212> TYPE: DNA
<213> ORGANISM: Artificial
<220> FEATURE:
<223> OTHER INFORMATION: DNA sequence of signal peptide SP15

<400> SEQUENCE: 15
atgaaacgta gcgattatat gttggcggca ctcgcctcag ccgtcctgcc gaatctgggg      60
gtggccggcg tacgcgagaa cgtgcaggcc agcgcaaccg acgaggccaa aggcatcgat     120
cagaccgtga ttcaagatgc ctcaggcaag                                      150

<210> SEQ ID NO 16
<211> LENGTH: 195
<212> TYPE: DNA
<213> ORGANISM: Artificial
<220> FEATURE:
<223> OTHER INFORMATION: DNA sequence of signal peptide SP16
```

<400> SEQUENCE: 16

| ttggcaagat gggtcactcg gagcgttccg gcaacggcct gtacgtcaac gtgcccggca | 60 |
| acaagtacca gccgatcttc gaggccggcg tggaatactt caccgcctga taatcggcgc | 120 |
| gtatcgcgtc tgatacggca cacagggaag gaactctcgg gttccttccc ttttttgttc | 180 |
| atgccggtca tgggc | 195 |

<210> SEQ ID NO 17
<211> LENGTH: 195
<212> TYPE: DNA
<213> ORGANISM: Artificial
<220> FEATURE:
<223> OTHER INFORMATION: DNA sequence of signal peptide SP19

<400> SEQUENCE: 17

| ttggcaagat gggtcactcg gagcgttccg gcaacggcct gtacgtcaac gtgcccggca | 60 |
| acaagtacca gccgatcttc gaggccggcg tggaatactt caccgcctga taatcggcgc | 120 |
| gtatcgcgtc tgatacggca cacagggaag gaactctcgg gttccttccc ttttttgttc | 180 |
| atgccggtca tgggc | 195 |

<210> SEQ ID NO 18
<211> LENGTH: 240
<212> TYPE: DNA
<213> ORGANISM: Artificial
<220> FEATURE:
<223> OTHER INFORMATION: DNA sequence of signal peptide SP21

<400> SEQUENCE: 18

| atggcattga ctgatgaaca ggtggagcgg tacgcgcgcc atctgatttt gaagggtgtg | 60 |
| ggggtcaaag gcaaaagcg gttgctggcc tccagcgtgc tcatcatcgg agcgggcggt | 120 |
| cttggttctc cggccgccct gtatctggcg gcggccggcg tcggccatat cggactggtg | 180 |
| gacggcgatg tggtggatat gagcaatctg caacgccaaa tcatccatac cactgcacgt | 240 |

<210> SEQ ID NO 19
<211> LENGTH: 240
<212> TYPE: DNA
<213> ORGANISM: Artificial
<220> FEATURE:
<223> OTHER INFORMATION: DNA sequence of signal peptide SP22

<400> SEQUENCE: 19

| ttggtgtcta tgagaagccc acgcgaggat tttgaggcgg caggcaagcg actgccttgg | 60 |
| gatgctgctg ctcgcagtgc agcgctgtcc gccaccgcgc cagtctctga cgtcaaggca | 120 |
| tccgccaatg gtgccgacaa tgccagcaac gctgaacatt ccgatgacat gcccaccgtg | 180 |
| ccgattcccg cacgcaaggc tgccacgacg ttcgacaccc cctccaagcg tgagcgcatc | 240 |

<210> SEQ ID NO 20
<211> LENGTH: 180
<212> TYPE: DNA
<213> ORGANISM: Artificial
<220> FEATURE:
<223> OTHER INFORMATION: DNA sequence of signal peptide SP23

<400> SEQUENCE: 20

| atgaacagc gatggaacaa actgtgtgtg tccgccctcg cctgcatggc gttggtcgtg | 60 |
| ccgttgaccg cctgtgaagg ccaactgccg acgccggctg ctgatacctc caccaaggtt | 120 |
| gcgccggatt tgaccgaggc gcaggagaag aagattcgtc tgaagattct caagacgatc | 180 |

<210> SEQ ID NO 21
<211> LENGTH: 180
<212> TYPE: DNA
<213> ORGANISM: Artificial
<220> FEATURE:
<223> OTHER INFORMATION: DNA sequence of signal peptide SP24

<400> SEQUENCE: 21
atggtcggca tgcgcgacgt agccaaagcg gcaggggtgt ccttaagcac cgtttcgttg    60
gtggtcaaca acaccggcta cgtctcggcc gatatgcgtg ccaaagtcga gtccgcgatg   120
cgccagctca actacattcc caacgagctg ccccgcaacc tctaccggaa ccgcaccaac   180

<210> SEQ ID NO 22
<211> LENGTH: 180
<212> TYPE: DNA
<213> ORGANISM: Artificial
<220> FEATURE:
<223> OTHER INFORMATION: DNA sequence of signal peptide SP25

<400> SEQUENCE: 22
gtgatgttat ccacaccctc cactacgttg ttttgcctcg cgctgggcag ccccacttca    60
gcaagagatt gcacagcttg cgttagggtg gagaacatga ctatcacagt atccacagac   120
ggttccgcat tagggaatcc aaacgggcca atgggctggg cctgggccga tcatgagcag   180

<210> SEQ ID NO 23
<211> LENGTH: 31
<212> TYPE: DNA
<213> ORGANISM: Artificial
<220> FEATURE:
<223> OTHER INFORMATION: forward primer for amplifying pCDshuttle

<400> SEQUENCE: 23
tcgaataacg ctttacaaac aattattaac g                                   31

<210> SEQ ID NO 24
<211> LENGTH: 33
<212> TYPE: DNA
<213> ORGANISM: Artificial
<220> FEATURE:
<223> OTHER INFORMATION: reverse primer for pCDshuttle

<400> SEQUENCE: 24
gacgactgga tccgtagaaa agatcaaagg atc                                 33

<210> SEQ ID NO 25
<211> LENGTH: 34
<212> TYPE: DNA
<213> ORGANISM: Artificial
<220> FEATURE:
<223> OTHER INFORMATION: forward primer for p37 insert

<400> SEQUENCE: 25
tacggatcca gtcgtcctcc caaactttgc agag                                34

<210> SEQ ID NO 26
<211> LENGTH: 38
<212> TYPE: DNA
<213> ORGANISM: Artificial
<220> FEATURE:
<223> OTHER INFORMATION: reverse primer for p37 insert

<400> SEQUENCE: 26

```
taaagcgtta ttcgacgccg agactttctt cttgggag                              38
```

<210> SEQ ID NO 27
<211> LENGTH: 29
<212> TYPE: DNA
<213> ORGANISM: Artificial
<220> FEATURE:
<223> OTHER INFORMATION: primer for p37

<400> SEQUENCE: 27

```
accatcatca ttgaccttct gctcgtagc                                        29
```

<210> SEQ ID NO 28
<211> LENGTH: 32
<212> TYPE: DNA
<213> ORGANISM: Artificial
<220> FEATURE:
<223> OTHER INFORMATION: primer for p37

<400> SEQUENCE: 28

```
cgagccggcg gccatattat ggttcttctt tc                                    32
```

<210> SEQ ID NO 29
<211> LENGTH: 262
<212> TYPE: DNA
<213> ORGANISM: Bifidobacterium longum

<400> SEQUENCE: 29

```
ctcccaaact tgcagagcc cgaccatcgt ggtcgggctt tttgtgttgt ccgggtggat        60
ttgcataata ggaaagcttg tgtctggaga ggagactcgc tagcacagca cagcaatata      120
agttgcggga ggagaccgac cacaggccga ttgcctacag catgcacgga taaataatga     180
gtcaagaccg agcatgatgg cagacagccg aacctgagga cggcgaccat tcgaaccgcg     240
ttatagaaag aagaaccata at                                              262
```

<210> SEQ ID NO 30
<211> LENGTH: 468
<212> TYPE: DNA
<213> ORGANISM: Artificial
<220> FEATURE:
<223> OTHER INFORMATION: hFGF codon optimized to bifidobacterium

<400> SEQUENCE: 30

```
atggccgccg gctcgatcac caccctgccg gccctgccgg aggatggcgg ctcgggcgcc      60
ttcccgccgg gccacttcaa ggacccgaag cgcctgtact gcaagaacgg cggcttcttc     120
ctgcgtatcc acccggacgg ccgtgtggat ggcgtccgtg agaagagcga cccgcatatc     180
aagctgcagc tgcaggccga ggaacgtggc gtggtctcca tcaagggcgt gtgcgccaac     240
cgctacctgg ccatgaagga agacggccgt ctgctggcct cgaagtgcgt caccgatgaa     300
tgcttcttct tcgagcgcct ggaatccaac aactacaaca cctaccgctc ccgtaagtac     360
accagctggt acgtggccct gaagcgtacc ggccagtaca agctgggcag caagaccggc     420
ccgggccaga aggccatcct gttcctgccg atgtccgcca gtcgtga                   468
```

<210> SEQ ID NO 31
<211> LENGTH: 43
<212> TYPE: DNA
<213> ORGANISM: Artificial
<220> FEATURE:
<223> OTHER INFORMATION: reverse primer for hFGF2 insert

<400> SEQUENCE: 31

```
gtcaatgatg atggtggtgg tgcgacttgg cggacatcgg cag            43
```

<210> SEQ ID NO 32
<211> LENGTH: 20
<212> TYPE: DNA
<213> ORGANISM: Artificial
<220> FEATURE:
<223> OTHER INFORMATION: forward primer for hFGF2 insert

<400> SEQUENCE: 32

```
atggccgccg gctcgatcac                                      20
```

<210> SEQ ID NO 33
<211> LENGTH: 4236
<212> TYPE: DNA
<213> ORGANISM: Artificial
<220> FEATURE:
<223> OTHER INFORMATION: hFGF2 expression plasmid

<400> SEQUENCE: 33

```
ggatccagtc gtcctcccaa actttgcaga gcccgaccat cgtggtcggg cttttgtgt      60
tgtccgggtg gatttgcata ataggaaagc ttgtgtctgg agaggagact cgctagcaca    120
gcacagcaat ataagttgcg ggaggagacc gaccacaggc cgattgccta cagcatgcac    180
ggataaataa tgagtcaaga ccgagcatga tggcagacag ccgaacctga ggacggcgac    240
cattcgaacc gcgttataga aagaagaacc ataatatggc cgccggctcg atcaccaccc    300
tgccggccct gccggaggat ggcggctcgg gcgccttccc gccgggccac ttcaaggacc    360
cgaagcgcct gtactgcaag aacggcggct tcttcctgcg tatccacccg gacggccgtg    420
tggatggcgt ccgtgagaag agcgacccgc atatcaagct gcagctgcag gccgaggaac    480
gtggcgtggt ctccatcaag ggcgtgtgcg ccaaccgcta cctggccatg aaggaagacg    540
gccgtctgct ggcctcgaag tgcgtcaccg atgaatgctt cttcttcgag cgcctggaat    600
ccaacaacta caacacctac cgctcccgta agtacaccag ctggtacgtg gccctgaagc    660
gtaccggcca gtacaagctg ggcagcaaga ccggcccggg ccagaaggcc atcctgttcc    720
tgccgatgtc cgccaagtcg caccaccacc atcatcattg accttctgct cgtagcgatt    780
acttcgagca ttactgacga caaagacccc gaccgagatg gtcggggtct ttttgttgtg    840
gtgctgtgac gtgttgtcca accgtattat tccggactag tcctccagga cctcgtctac    900
gaggcgctga gcgaggaatg cgcaaaagg gacggcgaga tcagcgaccc atgggccaac    960
gacgaggcga acggatacca gccgccctca tacgagccgg tcaaccccga acgcaggact   1020
ccccagacgc cctccgatgg cctgatctga cgtccgaaaa aaggcgctgt gcgccctttt   1080
taaatctttt ataaatcttt ttacattctt ttagcccctc cgcagcctta ctctcccaac   1140
gggtttcagc cgaaacctac accaaaaggg gagcgaacct acaccaaaag gggagcgaac   1200
ctacaccaaa aggggagcga acctacacca aaagggagc tatatacacc ttttgttatt   1260
taaggtgcaa gttgtgctat gctgaggcca tgtccaatga gatcgtgaag ttcagcaacc   1320
agttcaacaa cgtcgcgctg aagaagttcg acgccgtgca cctggacgtg ctcatggcga   1380
tcgcctcaag ggtgagggag aagggcacgg ccacggtgga gttctcgttc gaggagctgc   1440
gcggcctcat gcgattgagg aagaacctga ccaacaagca gctggccgac aagatcgtgc   1500
agacgaacgc gcgcctgctg cgcctgaact acatgttcga ggattcgggc aagatcatcc   1560
agttcgcgct gttcacgaag ttcgtcaccg acccgcagga ggcgactctc gcggttgggg   1620
```

```
tcaacgagga gttcgcgttc ctgctcaacg acctgaccag ccagttcacg cgcttcgagc    1680
tggccgagtt cgccgacctc aagagcaagt acgccaagga gttctaccgc agggccaagc    1740
agtaccgcag ctccggaatc tggaagatcg gccgcgacga gttctgccga ctgcttggcg    1800
ttccaccgtc ggcaataacc cagacacgat atctgaatca aaggttcttc agccaattc     1860
aggaggagtg tgggcctctc cttggcctga agatcgagcg ccagtacgtg aaacgcaggc    1920
tgtcgggctt cgtgttcaca ttcgcccgcg agacccctcc ggtgatcgac gccaggcccg    1980
tggaggcgag gaagacggac ggcgacggca agggccattg gacgagcgtt gccgggtacg    2040
gcgaggtgtt cacgaccacg cgcgttgttc gacgtgacgg ccgcccgggct cacttcgacg   2100
gcaccgttga agccggggag tgccgtttct gcgcgtttga cgcgcgcaac cgcgaacatc    2160
atgcgcggaa cgccggaagg ctgttctagc ggccgtgtcc gcgcctctgg ggcggttgcg    2220
cctgccatgg gtcgatctgc cgctgttcgg cctcacgctg gtctgtgcgc tgcctgatct    2280
ccctgagcag gtcggccttg gtcctggggg cgcttcgctc ctcgaacggg ccgctctccc    2340
ccaggtcctc gggctcgctc aggtccaacg gctcgtcacc ggacggctcg ggccggttct    2400
ctccctgtgc cgggttctcc gcctgtgcgc gttgttcggc catgcgcagt gcgagggcct    2460
tcacctgttc ggggcttgtc gactcgattt tcgttcgtga atacatgtta taataactat    2520
aactaataac gtaacgtgac tggcaagaga tatttttaaa acaatgaata ggtttacact    2580
tactttagtt ttatggaaat gaaagatcat atcatatata atctagaata aaattaacta    2640
aaataattat tatctagata aaaaatttag aagccaatga aatctataaa taaactaaat    2700
taagtttatt taattaacaa ctatggatat aaaataggta ctaatcaaaa tagtgaggag    2760
gatatatttg aatacatacg aacaaattaa taaagtgaaa aaaatacttc ggaaacattt    2820
aaaaaataac cttattggta cttacatgtt tggatcagga gttgagagtg gactaaaacc    2880
aaatagtgat cttgactttt tagtcgtcgt atctgaacca ttgacagatc aaagtaaaga    2940
aatacttata caaaaaatta gacctatttc aaaaaaaata ggagataaaa gcaacttacg    3000
atatattgaa ttaacaatta ttattcagca agaaatggta ccgtggaatc atcctcccaa    3060
acaagaattt atttatggag aatggttaca agagctttat gaacaaggat acattcctca    3120
gaaggaatta aattcagatt taaccataat gctttaccaa gcaaaacgaa aaaataaaag    3180
aatatacgga aattatgact tagaggaatt actacctgat attccatttt ctgatgtgag    3240
aagagccatt atggattcgt cagaggaatt aatagataat tatcaggatg atgaaaccaa    3300
ctctatatta actttatgcc gtatgatttt aactatggac acgggtaaaa tcataccaaa    3360
agatattgcg ggaaatgcag tggctgaatc ttctccatta gaacataggg agagaatttt    3420
gttagcagtt cgtagttatc ttggagagaa tattgaatgg actaatgaaa atgtaaattt    3480
aactataaac tatttaaata acagattaaa aaaattataa aaaaattgaa aaaatggtgg    3540
aaacactttt ttcaattttt ttagatcttg agcaaaaggc cagcaaaagg ccaggaaccg    3600
taaaaaggcc gcgttgctgg cgttttttcca taggctccgc cccccttgacg agcatcacaa    3660
aaatcgacgc tcaagtcaga ggtggcgaaa cccgacagga ctataaagat accaggcgtt    3720
tcccctggaa gctccctcg tgcgctctcc tgttccgacc ctgccgctta ccggatacct    3780
gtccgccttt ctcccttcgg gaagcgtggc gctttctcat agctcacgct gtaggtatct    3840
cagttcggtg taggtcgttc gctccaagct gggctgtgtg cacgaacccc ccgttcagcc    3900
cgaccgctgc gccttatccg gtaactatcg tcttgagtcc aacccggtaa gacacgactt    3960
atcgccactg gcagcagcca ctggtaacag gattagcaga gcgaggtatg taggcggtgc    4020
```

```
tacagagttc ttgaagtggt ggcctaacta cggctacact agaagaacag tatttggtat   4080
ctgcgctctg ctgaagccag ttaccttcgg aaaaagagtt ggtagctctt gatccggcaa   4140
acaaaccacc gctggtagcg gtggttttttt tgtttgcaag cagcagatta cgcgcagaaa   4200
aaaaggatct caagaagatc ctttgatctt ttctac                             4236
```

<210> SEQ ID NO 34
<211> LENGTH: 24
<212> TYPE: DNA
<213> ORGANISM: Artificial
<220> FEATURE:
<223> OTHER INFORMATION: primer for pFGF-P37

<400> SEQUENCE: 34

```
gccgccggct cgatcaccac cctg                                            24
```

<210> SEQ ID NO 35
<211> LENGTH: 28
<212> TYPE: DNA
<213> ORGANISM: Artificial
<220> FEATURE:
<223> OTHER INFORMATION: primer for pFGF-P37

<400> SEQUENCE: 35

```
catattatgg ttcttctttc tataacgc                                        28
```

<210> SEQ ID NO 36
<211> LENGTH: 39
<212> TYPE: DNA
<213> ORGANISM: Artificial
<220> FEATURE:
<223> OTHER INFORMATION: forward primer for signal peptide

<400> SEQUENCE: 36

```
aagaaccata atatggagca catgaagatg ttccggcac                            39
```

<210> SEQ ID NO 37
<211> LENGTH: 33
<212> TYPE: DNA
<213> ORGANISM: Artificial
<220> FEATURE:
<223> OTHER INFORMATION: reverse primer for signal peptide

<400> SEQUENCE: 37

```
gatcgagccg gcggccaatg ccacccaatc cgg                                  33
```

<210> SEQ ID NO 38
<211> LENGTH: 4377
<212> TYPE: DNA
<213> ORGANISM: Artificial
<220> FEATURE:
<223> OTHER INFORMATION: transformation plasmid pFGF12a

<400> SEQUENCE: 38

```
ggatccagtc gtcctcccaa actttgcaga gcccgaccat cgtggtcggg cttttttgtgt    60 tgtccgggtg gatttgcata ataggaaagc ttgtgtctgg agaggagact cgctagcaca    120
gcacagcaat ataagttgcg ggaggagacc gaccacaggc cgattgccta cagcatgcac    180
ggataaataa tgagtcaaga ccgagcatga tggcagacag ccgaacctga ggacggcgac    240
cattcgaacc gcgttataga aagaagaacc ataatatgga gcacatgaag atgttccggc    300
acctatcctc cgttttttgct attgcgacca ttgcgccgct ggcgttggcg gccacgctag    360
```

```
ccgtgacgcc tgcaatcgca caggccgacc agctgcccaa cccggattgg gtggcattgg      420
ccgccggctc gatcaccacc ctgccggccc tgccggagga tggcggctcg ggcgccttcc      480
cgccgggcca cttcaaggac ccgaagcgcc tgtactgcaa gaacggcggc ttcttcctgc      540
gtatccaccc ggacgccgt  gtggatggcg tccgtgagaa gagcgacccg catatcaagc      600
tgcagctgca ggccgaggaa cgtggcgtgg tctccatcaa gggcgtgtgc gccaaccgct      660
acctggccat gaaggaagac ggccgtctgc tggcctcgaa gtgcgtcacc gatgaatgct      720
tcttcttcga gcgcctggaa tccaacaact acaacaccta ccgctcccgt aagtacacca      780
gctggtacgt ggccctgaag cgtaccggcc agtacaagct gggcagcaag accgcccgg      840 gccagaaggc catcctgttc ctgccgatgt ccgccaagtc gcaccaccac catcatcatt      900
gaccttctgc tcgtagcgat tacttcgagc attactgacg acaaagaccc cgaccgagat      960
ggtcggggtc ttttgttgt ggtgctgtga cgtgttgtcc aaccgtatta ttccggacta     1020
gtcctccagg acctcgtcta cgaggcgctg agcgaggaat ggcgcaaaag ggacggcgag     1080
atcagcgacc catgggccaa cgacgaggcg gacggatacc agccgccctc atacgagccg     1140
gtcaaccccg aacgcaggac tccccagacg ccctccgatg gcctgatctg acgtccgaaa     1200
aaaggcgctg tgcgcccttt ttaaatcttt tataaatctt tttacattct tttagccct      1260 ccgcagcctt actctcccaa cgggtttcag ccgaaaccta caccaaaagg ggagcgaacc     1320
tacaccaaaa ggggagcgaa cctacaccaa aaggggagcg aacctacacc aaaaggggag     1380
ctatatacac cttttgttat ttaaggtgca agttgtgcta tgctgaggcc atgtccaatg     1440
agatcgtgaa gttcagcaac cagttcaaca acgtcgcgct gaagaagttc gacgccgtgc     1500
acctggacgt gctcatggcg atcgcctcaa gggtgaggga gaagggcacg gccacggtgg     1560
agttctcgtt cgaggagctg cgcggcctca tgcgattgag gaagaacctg accaacaagc     1620
agctggccga caagatcgtg cagacgaacg cgcgcctgct ggcgctgaac tacatgttcg     1680
aggattcggg caagatcatc cagttcgcgc tgttcacgaa gttcgtcacc gacccgcagg     1740
aggcgactct cgcggttggg gtcaacgagg agttcgcgtt cctgctcaac gacctgacca     1800
gccagttcac gcgcttcgag ctggccgagt tcgccgacct caagagcaag tacgccaagg     1860
agttctaccg cagggccaag cagtaccgca gctccggaat ctggaagatc ggccgcgacg     1920
agttctgccg actgcttggc gttccaccgt cggcaataac ccagacacga tatctgaatc     1980
agaaggttct tcagccaatt caggaggagt gtgggcctct ccttggcctg aagatcgagc     2040
gccagtacgt gaaacgcagg ctgtcgggct tcgtgttcac attcgcccgc gagacccctc     2100
cggtgatcga cgccaggccc gtggaggcga ggaagacgga cggcgacggc aagggccatt     2160
ggacgagcgt tgccgggtac ggcgaggtgt tcacgaccac ggcgttgttc gacgtgacgg     2220
ccgcccgggc tcacttcgac ggcaccgttg aagccgggga gtgccgtttc tgcgcgtttg     2280
acgcgcgcaa ccgcgaacat catgcgcgga acgccggaag gctgttctag cggccgtgtc     2340
cgcgcctctg gggcggttgc gcctgccatg ggtcgatctg ccgctgttcg gcctcacgct     2400
ggtctgtgcg ctgcctgatc tccctgagca ggtcggcctt ggtcctgggg gcgcttcgct     2460
cctcgaacgg gccgctctcc cccaggtcct cgggctcgct caggtccaac ggctcgtcac     2520
cggacggctc gggccggttc tctccctgtg ccgggttctc cgcctgtgcg cgttgttcgg     2580
ccatgcgcag tgcgagggcc ttcacctgtt cggggcttgt cgactcgatt ttcgttcgtg     2640
aatacatgtt ataataacta taactaataa cgtaacgtga ctggcaagag atattttaa      2700 aacaatgaat aggtttacac ttactttagt tttatggaaa tgaaagatca tatcatatat     2760
```

```
aatctagaat aaaattaact aaaataatta ttatctagat aaaaaattta gaagccaatg    2820
aaatctataa ataaactaaa ttaagtttat ttaattaaca actatggata taaaataggt    2880
actaatcaaa atagtgagga ggatatattt gaatacatac gaacaaatta ataaagtgaa    2940
aaaaatactt cggaaacatt taaaaaataa ccttattggt acttacatgt ttggatcagg    3000
agttgagagt ggactaaaac caaatagtga tcttgacttt ttagtcgtcg tatctgaacc    3060
attgacagat caaagtaaag aaatacttat acaaaaaatt agacctattt caaaaaaaat    3120
aggagataaa agcaacttac gatatattga attaacaatt attattcagc aagaaatggt    3180
accgtggaat catcctccca aacaagaatt tatttatgga gaatggttac aagagcttta    3240
tgaacaagga tacattcctc agaaggaatt aaattcagat ttaaccataa tgctttacca    3300
agcaaaacga aaaaataaaa gaatatacga aaattatgac ttagaggaat tactacctga    3360
tattccattt tctgatgtga gaagagccat tatggattcg tcagaggaat aatagataa    3420 ttatcaggat gatgaaacca actctatatt aactttatgc cgtatgattt taactatgga    3480
cacgggtaaa atcataccaa agatattgc gggaaatgca gtggctgaat cttctccatt    3540
agaacatagg gagagaattt tgttagcagt tcgtagttat cttggagaga atattgaatg    3600
gactaatgaa aatgtaaatt taactataaa ctatttaaat aacagattaa aaaaattata    3660
aaaaaattga aaaatggtg gaaacacttt tttcaatttt tttagatctt gagcaaaagg    3720
ccagcaaaag gccaggaacc gtaaaaaggc cgcgttgctg gcgttttttcc ataggctccg    3780 ccccctgac gagcatcaca aaaatcgacg ctcaagtcag aggtggcgaa acccgacagg    3840
actataaaga taccaggcgt ttccccctgg aagctccctc gtgcgctctc ctgttccgac    3900
cctgccgctt accggatacc tgtccgcctt tctcccttcg ggaagcgtgg cgctttctca    3960
tagctcacgc tgtaggtatc tcagttcggt gtaggtcgtt cgctccaagc tgggctgtgt    4020
gcacgaaccc cccgttcagc ccgaccgctg cgccttatcc ggtaactatc gtcttgagtc    4080
caacccggta agacacgact tatcgccact ggcagcagcc actggtaaca ggattagcag    4140
agcgaggtat gtaggcggtg ctacagagtt cttgaagtgg tggcctaact acggctacac    4200
tagaagaaca gtatttggta tctgcgctct gctgaagcca gttaccttcg gaaaaagagt    4260
tggtagctct tgatccggca aacaaaccac cgctggtagc ggtggttttt tgtttgcaa    4320 gcagcagatt acgcgcagaa aaaaaggatc tcaagaagat cctttgatct tttctac     4377
```

<210> SEQ ID NO 39
<211> LENGTH: 5058
<212> TYPE: DNA
<213> ORGANISM: Artificial
<220> FEATURE:
<223> OTHER INFORMATION: p37 plasmid

<400> SEQUENCE: 39

```
ggatccagtc gtcctcccaa actttgcaga gcccgaccat cgtggtcggg cttttttgtgt      60 tgtccgggtg gatttgcata ataggaaagc ttgtgtctgg agaggagact cgctagcaca     120
gcacagcaat ataagttgcg ggaggagacc gaccacaggc cgattgccta cagcatgcac     180
ggataaataa tgagtcaaga ccgagcatga tggcagacag ccgaacctga ggacggcgac     240
cattcgaacc gcgttataga agaagaacc ataatatggc tcccaagaag aaagtctcgg     300
cgtcgaataa cgctttacaa acaattatta cgcccggtt accaggcgaa gaggggctgt     360
ggcagattca tctgcaggac ggaaaaatca gcgccattga tgcgcaatcc ggcgtgatgc     420
```

```
ccataactga aaacagcctg gatgccgaac aaggtttagt tataccgccg tttgtggagc    480
cacatattca cctggacacc acgcaaaccg ccggacaacc gaactggaat cagtccggca    540
cgctgtttga aggcattgaa cgctgggccg agcgcaaagc gttattaacc catgacgatg    600
tgaaacaacg cgcatggcaa acgctgaaat ggcagattgc caacggcatt cagcatgtgc    660
gtacccatgt cgatgtttcg gatgcaacgc taactgcgct gaaagcaatg ctggaagtga    720
agcaggaagt cgcgccgtgg attgatctgc aaatcgtcgc cttccctcag gaagggattt    780
tgtcgtatcc caacggtgaa gcgttgctgg aagaggcgtt acgcttaggg gcagatgtag    840
tgggggcgat tccgcatttt gaatttaccc gtgaatacgg cgtggagtcg ctgcataaaa    900
ccttcgccct ggcgcaaaaa tacgaccgtc tcatcgacgt tcactgtgat gagatcgatg    960
acgagcagtc gcgctttgtc gaaaccgttg ctgccctggc gcaccatgaa ggcatgggcg   1020
cgcgagtcac cgccagccac accacggcaa tgcactccta taacggggcg tatacctcac   1080
gcctgttccg cttgctgaaa atgtccggta ttaactttgt cgccaacccg ctggtcaata   1140
ttcatctgca aggacgtttc gatacgtatc caaaacgtcg cggcatcacg cgcgttaaag   1200
agatgctgga gtccggcatt aacgtctgct ttggtcacga tgctgtcttc gatccgtggt   1260
atccgctggg aacggcgaat atgctgcaag tgctgcatat ggggctgcat gtttgccagt   1320
tgatgggcta cggcagatt aacgatggcc tgaatttaat cacccaccac agcgcaagga   1380
cgttgaattt gcaggattac ggcattgccg ccggaaacag cgccaacctg attatcctgc   1440
cggctgaaaa tgggtttgat gcgctgcgcc gtcaggttcc ggtacgttat tcggtacgtg   1500
gcggcaaggt gattgccagc acacaaccgg cacaaaccac cgtatatctg gagcagccag   1560
aagccatcga ttacaaacgt tgaccttctg ctcgtagcga ttacttcgag cattactgac   1620
gacaaagacc ccgaccgaga tggtcggggt cttttgttg tggtgctgtg acgtgttgtc   1680
caaccgtatt attccggact agtcctccag gacctcgtct acgaggcgct gagcgaggaa   1740
tggcgcaaaa gggacggcga gatcagcgac ccatgggcca acgacgaggc ggacggatac   1800
cagccgccct catacgagcc ggtcaacccc gaacgcagga ctccccagac gccctccgat   1860
ggcctgatct gacgtccgaa aaaggcgct gtgcgccctt tttaaatctt ttataaatct   1920
ttttacattc ttttagcccc tccgcagcct tactctccca acgggtttca gccgaaacct   1980
acaccaaaag gggagcgaac ctacaccaaa aggggagcga acctacacca aaagggggagc   2040
gaacctacac caaaagggga gctatataca ccttttgtta tttaaggtgc aagttgtgct   2100
atgctgaggc catgtccaat gagatcgtga agttcagcaa ccagttcaac aacgtcgcgc   2160
tgaagaagtt cgacgccgtg cacctggacg tgctcatggc gatcgcctca agggtgaggg   2220
agaagggcac ggccacggtg gagttctcgt tcgaggagct cgcggcctc atgcgattga   2280
ggaagaacct gaccaacaag cagctggccg acaagatcgt gcagacgaac gcgcgcctgc   2340
tggcgctgaa ctacatgttc gaggattcgg gcaagatcat ccagttcgcg ctgttcacga   2400
agttcgtcac cgacccgcag gaggcgactc tcgcggttgg ggtcaacgag gagttcgcgt   2460
tcctgctcaa cgacctgacc agccagttca cgcgcttcga gctggccgag ttcgccgacc   2520
tcaagagcaa gtacgccaag gagttctacc gcagggccaa gcagtaccgc agctccggaa   2580
tctggaagat cggccgcgac gagttctgcc gactgcttgg cgttccaccg tcggcaataa   2640
cccagacacg atatctgaat cagaaggttc ttcagccaat tcaggaggag tgtgggcctc   2700
tccttggcct gaagatcgag cgccagtacg tgaaacgcag gctgtcgggc ttcgtgttca   2760
cattcgcccg cgagacccct ccggtgatcg acgccaggcc cgtggaggcg aggaagacgg   2820
```

```
acggcgacgg caagggccat tggacgagcg ttgccgggta cggcgaggtg ttcacgacca    2880
cggcgttgtt cgacgtgacg gccgcccggg ctcacttcga cggcaccgtt gaagccgggg    2940
agtgccgttt ctgcgcgttt gacgcgcgca accgcgaaca tcatgcgcgg aacgccggaa    3000
ggctgttcta gcgccgtgt ccgcgcctct ggggcggttg cgcctgccat gggtcgatct    3060
gccgctgttc ggcctcacgc tggtctgtgc gctgcctgat ctccctgagc aggtcggcct    3120
tggtcctggg ggcgcttcgc tcctcgaacg ggccgctctc ccccaggtcc tcgggctcgc    3180
tcaggtccaa cggctcgtca ccggacggct cgggccggtt ctctccctgt gccgggttct    3240
ccgcctgtgc gcgttgttcg gccatgcgca gtgcgagggc cttcacctgt tcggggcttg    3300
tcgactcgat tttcgttcgt gaatacatgt tataataact ataactaata acgtaacgtg    3360
actggcaaga gatatttta aaacaatgaa taggtttaca cttactttag ttttatggaa    3420
atgaaagatc atatcatata taatctagaa taaaattaac taaataatt attatctaga    3480
taaaaatttt agaagccaat gaaatctata aataaactaa attaagttta tttaattaac    3540
aactatggat ataaaatagg tactaatcaa aatagtgagg aggatatatt tgaatacata    3600
cgaacaaatt aataaagtga aaaaaatact tcggaaacat ttaaaaaata accttattgg    3660
tacttacatg tttggatcag gagttgagag tggactaaaa ccaaatagtg atcttgactt    3720
tttagtcgtc gtatctgaac cattgacaga tcaaagtaaa gaaatactta tacaaaaaat    3780
tagacctatt tcaaaaaaaa taggagataa aagcaactta cgatatattg aattaacaat    3840
tattattcag caagaaatgg taccgtggaa tcatcctccc aaacaagaat ttatttatgg    3900
agaatggtta caagagcttt atgaacaagg atacattcct cagaaggaat taaattcaga    3960
tttaaccata atgctttacc aagcaaaacg aaaaaataaa agaatatacg gaattatga    4020
cttagaggaa ttactacctg atattccatt ttctgatgtg agaagagcca ttatggattc    4080
gtcagaggaa ttaatagata attatcagga tgatgaaacc aactctatat taactttatg    4140
ccgtatgatt ttaactatgg acacgggtaa aatcatacca aaagatattg cgggaaatgc    4200
agtggctgaa tcttctccat tagaacatag ggagagaatt ttgttagcag ttcgtagtta    4260
tcttggagag aatattgaat ggactaatga aaatgtaaat ttaactataa actatttaaa    4320
taacagatta aaaaaattat aaaaaaattg aaaaaatggt ggaaacactt tttcaatttt    4380
ttttagatct tgagcaaaag gccagcaaaa ggccaggaac cgtaaaaagg ccgcgttgct    4440
ggcgtttttc cataggctcc gccccctga cgagcatcac aaaaatcgac gctcaagtca    4500
gaggtggcga aacccgacag gactataaag ataccaggcg tttccccctg gaagctccct    4560
cgtgcgctct cctgttccga ccctgccgct taccggatac ctgtccgcct ttctccctc    4620
gggaagcgtg gcgctttctc atagctcacg ctgtaggtat ctcagttcgg tgtaggtcgt    4680
tcgctccaag ctgggctgtg tgcacgaacc ccccgttcag cccgaccgct gcgccttatc    4740
cggtaactat cgtcttgagt ccaacccggt aagacacgac ttatcgccac tggcagcagc    4800
cactggtaac aggattagca gagcgaggta tgtaggcggt gctacagagt tcttgaagtg    4860
gtggcctaac tacggctaca ctagaagaac agtatttggt atctgcgctc tgctgaagcc    4920
agttaccttc ggaaaagag ttggtagctc ttgatccggc aaacaaacca ccgctggtag    4980
cggtggtttt tttgtttgca agcagcagat tacgcgcaga aaaaaggat ctcaagaaga    5040
tcctttgatc ttttctac                                                 5058
```

```
<210> SEQ ID NO 40
<211> LENGTH: 208
<212> TYPE: PRT
<213> ORGANISM: Artificial
<220> FEATURE:
<223> OTHER INFORMATION: polypeptide coded by pFGF12a

<400> SEQUENCE: 40

Met Glu His Met Lys Met Phe Arg His Leu Ser Ser Val Phe Ala Ile
1               5                   10                  15

Ala Thr Ile Ala Pro Leu Ala Leu Ala Ala Thr Leu Ala Val Thr Pro
            20                  25                  30

Ala Ile Ala Gln Ala Asp Gln Leu Pro Asn Pro Asp Trp Val Ala Leu
        35                  40                  45

Ala Ala Gly Ser Ile Thr Thr Leu Pro Ala Leu Pro Glu Asp Gly Gly
    50                  55                  60

Ser Gly Ala Phe Pro Pro Gly His Phe Lys Asp Pro Lys Arg Leu Tyr
65                  70                  75                  80

Cys Lys Asn Gly Gly Phe Phe Leu Arg Ile His Pro Asp Gly Arg Val
                85                  90                  95

Asp Gly Val Arg Glu Lys Ser Asp Pro His Ile Lys Leu Gln Leu Gln
            100                 105                 110

Ala Glu Glu Arg Gly Val Val Ser Ile Lys Gly Val Cys Ala Asn Arg
        115                 120                 125

Tyr Leu Ala Met Lys Glu Asp Gly Arg Leu Leu Ala Ser Lys Cys Val
    130                 135                 140

Thr Asp Glu Cys Phe Phe Phe Glu Arg Leu Glu Ser Asn Asn Tyr Asn
145                 150                 155                 160

Thr Tyr Arg Ser Arg Lys Tyr Thr Ser Trp Tyr Val Ala Leu Lys Arg
                165                 170                 175

Thr Gly Gln Tyr Lys Leu Gly Ser Lys Thr Gly Pro Gly Gln Lys Ala
            180                 185                 190

Ile Leu Phe Leu Pro Met Ser Ala Lys Ser His His His His His His
        195                 200                 205
```

THERAPEUTIC AGENT FOR ISCHEMIC DISEASES

RELATED APPLICATIONS

This application is a continuation-in-part of, and claims priority under 35 USC §120 to U.S. Ser. No. 13/548,544, filed Jul. 13, 2012, which is a continuation-in-part of, and claims priority under 35 USC §120 to, U.S. Ser. No. 13/015,806, filed Jan. 28, 2011, which claims priority under 35 USC 119(e) to U.S. Ser. No. 61/299,922 filed Jan. 29, 2010. Further, this application claims priority under 35 USC 119(e) to U.S. Ser. No. 61/507,590 filed Jul. 13, 2011. This application also is a continuation-in-part of, and claims priority under 35 USC §120 to, U.S. Ser. No. 13/749,428, filed Jan. 24, 2013, which is a divisional of U.S. Ser. No. 12/425,001, filed Apr. 16, 2009, which claims priority under 35 USC 119(e) to U.S. Ser. No. 61/124,528, filed Apr. 17, 2008. The disclosures of all of the above are hereby incorporated by reference in their entireties for all purposes.

TECHNICAL FIELD

The present invention relates to a gene transfer carrier and a pharmaceutical composition that can specifically treat the site of an ischemic disease, and a treatment method for an ischemic disease using same.

BACKGROUND ART

Recently, in the treatment of malignant tumors, a method in which a transformed anaerobic bacterium is used as a gene transfer carrier has been attracting attention; for example, a method in which a gene expressing a nitroreductase, which is an enzyme that converts a prodrug for an antitumor substance into the antitumor substance, is transported to a tumor site using a transformed clostridium has been proposed (ref. Patent Documents 1 to 3).

However, all of the microorganisms that have conventionally been used for the above-mentioned purpose are low toxicity mutants of pathogenic microbes, and the possibility of reverse mutation, with them returning to the original pathogenic microbes and exhibiting toxicity, cannot be ruled out; furthermore, due to mobility and invasiveness there is a possibility that the effect will be exhibited not only in diseased tissue but also in normal tissue to thus cause systemic side effect symptoms, and there is a problem in terms of safety.

Under such circumstances, *Bifidobacterium*, which is a nonpathogenic enterobacterium that is present within and makes up the flora in the human intestine and is known to be a very safe obligately anaerobic bacterium, has been attracting attention, and a transformed *Bifidobacterium* that expresses cytosine deaminase, which is an enzyme that converts 5-fluorocytosine, which is a prodrug for the antitumor substance 5-fluorouracil, into 5-FU has been developed (ref. Patent Documents 4 and 5).

This transformant *Bifidobacterium* has the advantage that when it is intravenously administered into an animal model of solid tumor which is an anaerobic disease, it specifically colonizes and grows in anaerobic diseased tissue in a low oxygen state and quickly disappears in normal tissue that is not in an anaerobic environment (ref. Non-Patent Documents 1 and 2).

In the meantime, in the treatment of an ischemic disease, in particular the treatment of a serious case of ischemia, an angiogenic therapy in which blood flow is restored by regeneration of blood vessels or development of collateral circulation has been attempted. Angiogenic therapy can be broadly divided into three types of therapies, that is, cell transplantation, protein administration, and gene therapy, but from the viewpoint of low invasiveness, gene therapy has particularly been attracting attention in recent years. In angiogenesis by gene therapy, for example, a gene coding for hepatocyte growth factor: HGF, vascular endothelial growth factor: VEGF, etc. is introduced into an area around an affected part by intramuscular injection or intraarterial infusion, thus promoting angiogenesis in the area around the affected part and thereby restoring blood flow (ref. e.g. Non-Patent Documents 3 and 4).

These angiogenesis therapies have been attracting attention as one option for a patient for whom revascularization is not possible or whom the effect is insufficient due to a disorder at the arteriolar level, or a patient who cannot be treated surgically due to a problem with invasiveness and, in particular, with regard to angiogenic therapy by gene therapy, many clinical tests have been carried out in recent years.

PRIOR ART DOCUMENTS

Patent Documents

[Patent Document 1] U.S. Pat. No. 6,416,754
[Patent Document 2] U.S. Pat. No. 6,652,849
[Patent Document 3] US. Pat. Application No. 2003/0103952
[Patent Document 4] JP, A, 2002-97144
[Patent Document 5] WO No. 2007-136107

Non-Patent Document

[Non-Patent Document 1] Yazawa et al., Cancer Gene Therapy, Vol. 7, No. 2, 2000: pp 269-274
[Non-Patent Document 2] Yazawa et al., Breast Cancer Research and Treatment, Vol. 66, 2001: pp 165-170
[Non-Patent Document 3] Gupta et al., Circ. Res. 2009; 105: 724-736
[Non-Patent Document 4] Morishita et al., Arterioscler Thromb Vasc Biol. 2011; 31: 713-720

SUMMARY OF THE INVENTION

Problems to be Solved by the Invention

It is an object of the present invention to provide a gene transfer carrier, formed from an anaerobic bacterium, that can grow specifically at the site of an ischemic disease and can express at least one type of protein that is useful for the diagnosis or treatment of an ischemic disease, a pharmaceutical composition containing the gene transfer carrier, and a treatment method for an ischemic disease utilizing same.

Means for Solving the Problems

As hereinabove described, although angiogenic therapy utilizing gene therapy is useful for the treatment of an ischemic disease, current angiogenic therapy utilizing gene therapy still has some problems. Firstly, currently used gene transfer carriers do not have lesion site specificity and when systemically administered they are systemically disseminated, therefore, intramuscular injection or intraarterial infusion is mainly used to administer a transgene; but in these administration methods it cannot be said that it is administered specifically and uniformly to the ischemic disease site and, furthermore, when an ischemic site and a non-ischemic site are present together, a large amount of transgene is delivered to the non-ischemic site, thereby angiogenesis in the non-ischemic site is promoted, and as a result a phenomenon called steal phenomenon in which blood circulation further deteriorates at the ischemic site might occur.

Secondly, since it is a treatment method predicated on a target protein being expressed at a disease site by gene transfection using a vector, it is difficult to control the efficiency of gene transfection or the period of transgene expression. There are therefore the problems that even if administered the transfection is not sufficient thereby an effect is not exhibited, transgene expression stops before remission of the disease, or transgene expression continues after remission.

Thirdly, it is thought that angiogenic therapy is greatly superior to other therapies for the elderly, diabetic patients, etc. because of low invasiveness, but these patients might have complications whose symptoms may be aggravated by angiogenesis, such as for example diabetic retinopathy in a diabetic patient or a malignant tumor in the elderly, and the application of current angiogenic therapy, which has low specificity for a disease site, is limited.

The present inventors have found that all of these problems can be solved by a vector that specifically accumulates only at a disease site even with systemic administration, has a high protein expression rate, and disappears from the disease site accompanying a cure, and as a result of an intensive investigation the present invention has been accomplished.

That is, the present invention relates to the following.
(1) A gene transfer carrier consisted of an anaerobic bacterium that can grow specifically at the site of an ischemic disease and can express at least one type of protein that is useful for the diagnosis or treatment of an ischemic disease.
(2) The gene transfer carrier according to (1), wherein the anaerobic bacterium is transformed using a transforming plasmid, said plasmid comprising a DNA sequence coding for the protein that is useful for the diagnosis or treatment of an ischemic disease.
(3) The gene transfer carrier according to (1) or (2), wherein the ischemic disease is a chronic ischemic disease.
(4) The gene transfer carrier according to (1) to (3), wherein the anaerobic bacterium is a nonpathogenic enterobacterium.
(5) The gene transfer carrier according to (1) to (4), wherein the anaerobic bacterium is a *Bifidobacterium*.
(6) The gene transfer carrier according to (5), wherein the *Bifidobacterium* is one type selected from the group consisting of *Bifidobacterium adolescentis, Bifidobacterium angulatum, Bifidobacterium animalis, Bifidobacterium asteroides, Bifidobacterium bifidum, Bifidobacterium bourn, Bifidobacterium breve, Bifidobacterium catenulatum, Bifidobacterium choerinum, Bifidobacterium coryneforme, Bifidobacterium cuniculi, Bifidobacterium denticolens, Bifidobacterium dentium, Bifidobacterium gallicum, Bifidobacterium gallinarum, Bifidobacterium globosum, Bifidobacterium indicum, Bifidobacterium infantis, Bifidobacterium inopinatum, Bifidobacterium lactis, Bifidobacterium lactentis, Bifidobacterium liberorum, Bifidobacterium longum, Bifidobacterium magnum, Bifidobacterium merycicum, Bifidobacterium minimum, Bifidobacterium mongoliens, Bifidobacterium parvulorum, Bifidobacterium pseudocatenulatum, Bifidobacterium pseudolongum, Bifidobacterium psychraerophilum, Bifidobacterium pullorum, Bifidobacterium ruminale, Bifidobacterium ruminantium, Bifidobacterium saeculare, Bifidobacterium scardovi, Bifidobacterium subtile, Bifidobacterium suis, Bifidobacterium thermacidophillum,* and *Bifidobacterium thermophilum*.
(7) The gene transfer carrier according to (6), wherein the *Bifidobacterium* is *Bifidobacterium longum*.
(8) The gene transfer carrier according to (1) to (7), wherein the protein that is useful for the diagnosis of an ischemic disease is a fluorescent protein.
(9) The gene transfer carrier according to (1) to (7), wherein the protein that is useful for the treatment of an ischemic disease is at least one type selected from the group consisting of fibroblast growth factor (FGF), endothelial cell growth factor (ECGF), vascular endothelium growth factor (VEGF), hepatocyte growth factor (HGF), angiogenic growth factor (AGF), platelet-derived growth factor (PDGF), transforming growth factor β (TGFβ), a protein having angiogenesis promoting activity such as angiopoietin or ephrin, a factor involved in vasodilation such as a prostaglandin, a colony stimulating factor such as granulocyte colony stimulating factor (G-CSF) or granulocyte-macrophage colony stimulating factor (GM-CSF), nerve growth factor (NGF), brain-derived neurotrophic factor (BDNF), a neurotrophin such as neurotrophin 3, and insulin-like growth factor (IGF).
(10) The gene transfer carrier according to (2) to (9), wherein the transforming plasmid is a non-shuttle plasmid.
(11) The gene transfer carrier according to (2) to (10), wherein the transforming plasmid further comprises a gene sequence coding for a secretory signal peptide.
(12) The gene transfer carrier according to any one of (2) to (11), wherein the transforming plasmid comprises pTB6 rep unit.
(13) The gene transfer carrier according to any one of (2) to (12), wherein the transforming plasmid has an expression cassette comprising p37 promoter, HU terminator and a gene coding for FGF2.
(14) The gene transfer carrier according to any one of (2) to (13), wherein the transforming plasmid comprises a DNA sequence coding for a polypeptide having the sequence described in SEQ ID No: 40.
(15) The gene transfer carrier according to any one of (2) to (14), wherein the transforming plasmid is pFGF12a (SEQ ID No: 38).
(16) A pharmaceutical composition for an ischemic disease comprising the gene transfer carrier according to (1) to (15).
(17) The pharmaceutical composition according to (16), wherein it is administered by systemic administration.
(18) A method for diagnosing or treating an ischemic disease, the method comprising administering an anaerobic bacterium that can specifically grow at the site of an ischemic disease and can express at least one type of protein that is useful for the diagnosis or treatment of an ischemic disease.
(19) The method according to (18), wherein said administering is systemically administering.

Effects of the Invention

Since the gene transfer carrier of the present invention is an anaerobic bacterium, it colonizes and grows specifically at the site of an ischemic disease, which is under an anaerobic environment, can produce and secrete a protein having therapeutic activity for an ischemic disease in the diseased tissue, is very useful as a drug for the treatment of an ischemic disease, and can be expected to be a high quality gene transfer carrier. Furthermore, since it colonizes specifically at the site of an ischemic disease, it specifically accumulates at the site of an ischemic disease and exhibits an effect even with systemic administration such as intravenous injection. Therefore, there is no necessity for the administration of a large amount or administration multiple times, and the burden on the administration subject can be alleviated. Moreover, since the anaerobic environment at the site of the ischemic disease is maintained while the ischemia continues, it grows for a long period of time, but once the ischemia enters remission, the anaerobic environment is no longer maintained, it cannot grow and quickly disappears.

Furthermore, since the gene transfer carrier of the present invention can itself express a protein that is useful for treatment, it is not necessary to take into consideration the efficiency of gene transfer to the ischemic site or the cells in its vicinity as in the conventional art, and high protein expression efficiency can always be exhibited. Moreover, since it is a carrier that is specifically delivered to the ischemic site, there are no concerns about complications. It is therefore possible to carry out an angiogenic treatment that is less invasive than the conventional art, causes fewer side effects, and has high safety. Furthermore, making the gene transfer carrier of the present invention simultaneously express a marker enables it to be used for the diagnosis of an ischemic site or as a monitor for a treatment. Moreover, the gene carrier of the present invention can deliver a plurality of genes at the same time, and it is thought that a more efficient and noninvasive treatment will become possible by incorporating a plurality of effective growth factors and administering.

JCM1192 transformed with pBEshuttle is used as a negative control, and hFGF2 is used as a positive control. Again, a band of approximately 20 kDa was confirmed, being considered to be hFGF2.

Figure 19:
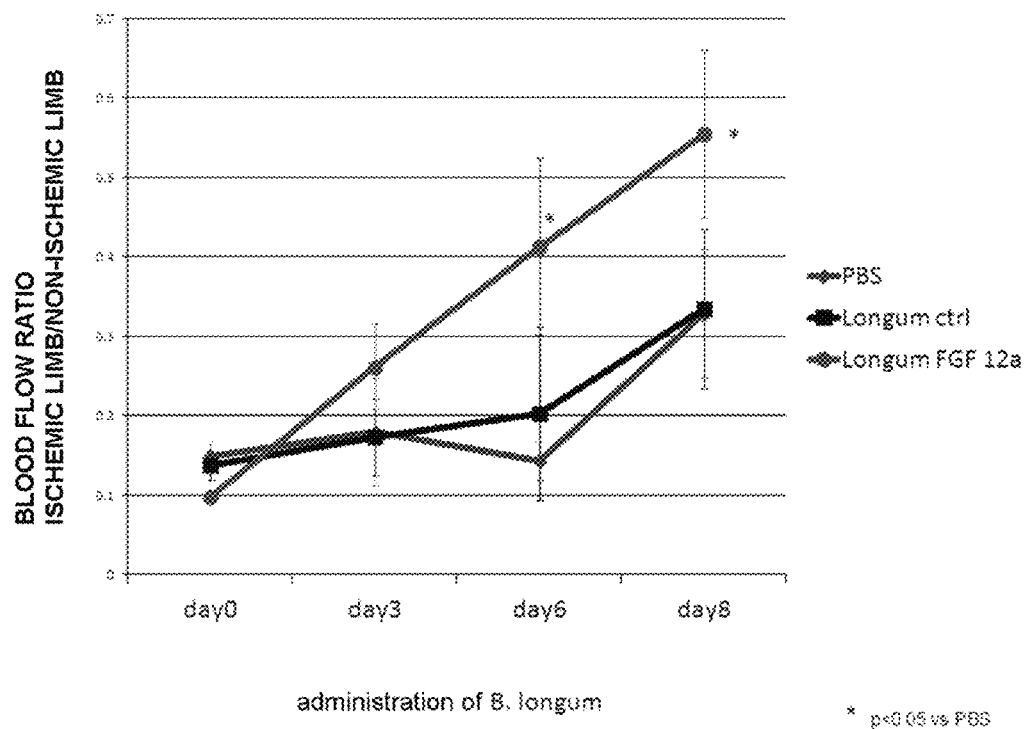

FIG. 19 is a graph showing changes in blood flow in lower limb ischemic site of ischemic model mice which had been given an intravenous injection of the pharmaceutical composition comprising *Bifidobacterium longum* 105A/pFGF12a, i.e., the gene transfer carrier of the invention. Though there was already a small difference in the recovery of blood flow on Day 3, a significant recovery of blood flow was observed after Day 6 in the group which had been treated with the gene transfer carrier of the invention.

Figure 20:
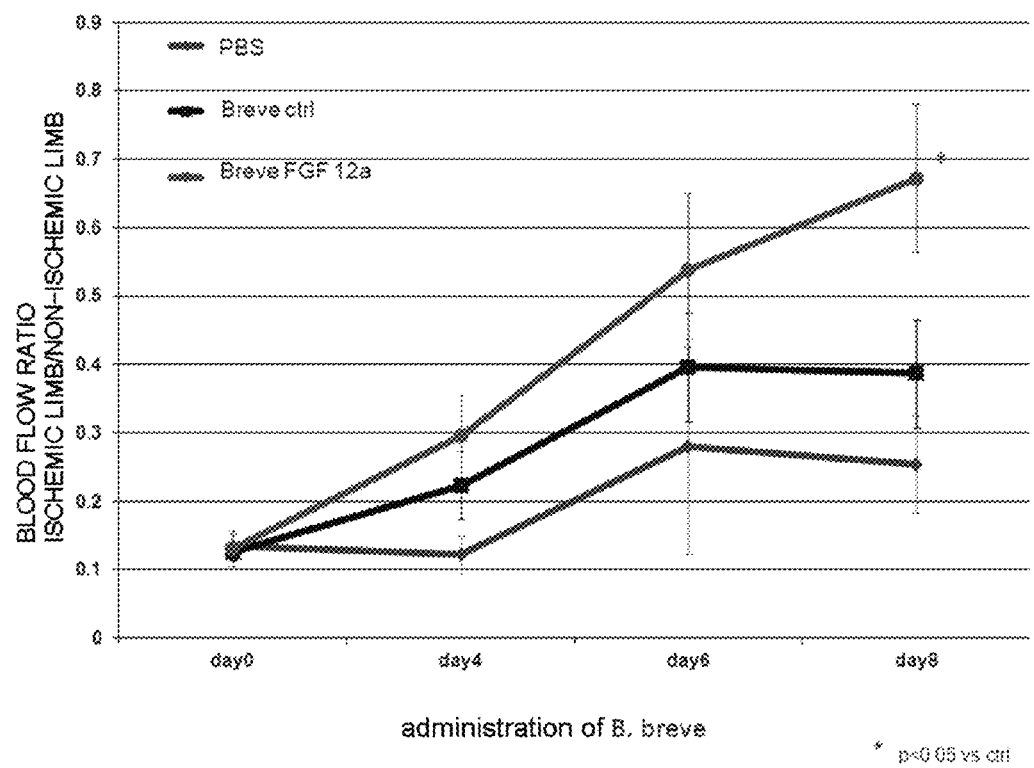

FIG. 20 is a graph showing changes in blood flow in lower limb ischemic site of ischemic model mice which had been given an intravenous injection of the pharmaceutical composition comprising *Bifidobacterium breve* JCM1192/pFGF12a, i.e., the gene transfer carrier of the invention. Though there was already a small difference in the recovery of blood flow on Day 4, a significant recovery of blood flow was observed after Day 8 in the group which had been treated with the gene transfer carrier of the invention.

MODES FOR CARRYING OUT THE INVENTION

The present invention relates to a gene transfer carrier formed from an anaerobic bacterium that can grow specifically at the site of an ischemic disease and can express at least one type of protein that is useful for the diagnosis or treatment of an ischemic disease.

In the present invention, 'ischemia' means a state in which there is a shortage of oxygen and nutrients in tissue due to a decrease in the amount of arterial blood supplied to the tissue caused by constriction or blockage of blood vessels, and persistent ischemia causes tissue atrophy, degeneration, necrosis, etc.

The gene transfer carrier of the present invention is mainly used in a treatment method for improving an undesirable state caused by ischemia, such as an angiogenic treatment or protection of an organ. Therefore, in the present specification, an 'ischemic disease' is a state in which, regardless of the presence or absence of subjective symptoms, ischemia of the tissue is sustained by the constriction or blockage of arteries or an undesirable state caused by such ischemia. Examples of the ischemic disease include, but are not limited to, an ischemic heart disease such as angina pectoris or myocardial infarction, a cerebral ischemia such as cerebral infarction, a chronic cerebral ischemia such as moyamoya disease, spinal ischemia, an ischemic bowel disease such as ischemic colitis or mesenteric arterial occlusion, a lower limb ischemia such as arteriosclerosis obliterans, and a retinal ischemia such as diabetic retinopathy.

In the present specification, 'ischemic site' means a site in a state in which there is a shortage of arterial blood flow, nutrients, and oxygen due to ischemia, and is used interchangeably with 'site of an ischemic disease' or 'ischemic diseased tissue'.

In the present specification, 'anaerobic bacterium' means a bacterium having anaerobic properties, and 'anaerobic properties' means the property of being capable of growing under conditions where there is little or no oxygen. Anaerobic bacteria can generally be classified into facultative anaerobic bacteria, which can grow in the presence of oxygen, and obligately anaerobic bacteria, which cannot grow in the presence of oxygen, and in the present invention obligately anaerobic bacteria are preferable. The anaerobic properties of the anaerobic bacterium of the present invention may be properties that the bacterium has intrinsically or those obtained by transformation.

Since the gene transfer carrier of the present invention is formed from an anaerobic bacterium, it can colonize and grow specifically at the site of an ischemic disease, which is under anaerobic conditions. Since the gene transfer carrier itself has gene transcription and translation functions, it can express a protein that is useful for diagnosis or treatment when it colonizes the ischemic diseased tissue, and can supply it to the diseased tissue. Therefore, the gene transfer carrier of the present invention comprises a DNA sequence coding for a protein that is useful for the diagnosis or treatment of an ischemic disease.

In one embodiment of the present invention, the gene transfer carrier is transformed by a transforming plasmid. Any transforming plasmid may be used as long as it functions in the gene transfer carrier bacterium and does not impair the anaerobic properties of the bacterium.

As described above, the anaerobic properties of the anaerobic bacterium that is the gene transfer carrier of the present invention may be those obtained by transformation, and in one embodiment of the present invention the anaerobic bacterium is transformed so as to be an obligately anaerobic bacterium.

In a preferred embodiment of the present invention, the gene transfer carrier is transformed by a plasmid having a DNA sequence coding for a protein that is useful for the diagnosis or treatment of an ischemic disease. Imparting by transformation an ability to express a protein that is useful for the diagnosis or treatment of an ischemic disease enables any protein to be expressed in accordance with the design of a plasmid.

In the present invention, the ischemic disease includes an acute ischemic disease in which tissue is damaged as a result of a rapid decrease of the oxygen concentration caused by ischemia, and a chronic ischemic disease in which denaturing or necrosis of tissue is caused by a low oxygen concentration sustained for a long period of time. Since the gene transfer carrier of the present invention is selectively delivered to a disease site after being administered, colonizes and remains at the delivery site, and exhibits an effect, it is preferably used for improvement of a chronic ischemic state. In the present specification, the term 'chronic ischemic state' is used interchangeably with the term 'chronic ischemic disease', and examples include, but are not limited to, an ischemic heart disease such as angina pectoris or myocardial infarction, a chronic cerebral ischemia such as moyamoya disease, and a lower limb ischemia such as arteriosclerosis obliterans. Examples of a treatment for improving a chronic ischemic disease include, but are not limited to, an angiogenic therapy.

Since it is assumed that the gene transfer carrier of the present invention is administered internally, it is necessary for the anaerobic bacterium that is used to have no toxicity or little toxicity. Therefore, in one embodiment of the present invention, the gene transfer carrier can be a mutant that is formed by mutating a pathogenic bacterium so that it has low toxicity. However, there is a possibility that a mutant bacterium having low toxicity will return to the original pathogenic microbe by reverse mutation and exhibit toxicity, and it is therefore preferable to use an intrinsically nonpathogenic bacterium. Therefore, in a preferred embodiment of the present invention, the anaerobic bacterium used is a nonpathogenic enterobacterium.

As the nonpathogenic enterobacterium that can be used in the present invention, a bacterium belonging to the *Bifido-*

*bacterium* genus (*Bifidobacterium*) can be cited. Examples of bacteria belonging to the *Bifidobacterium* genus include *Bifidobacterium adolescentis, Bifidobacterium angulatum, Bifidobacterium animalis, Bifidobacterium asteroides, Bifidobacterium bifidum, Bifidobacterium bourn, Bifidobacterium breve, Bifidobacterium catenulatum, Bifidobacterium choerinum, Bifidobacterium coryneforme, Bifidobacterium cuniculi, Bifidobacterium denticolens, Bifidobacterium dentium, Bifidobacterium gallicum, Bifidobacterium gallinarum, Bifidobacterium globosum, Bifidobacterium indicum, Bifidobacterium infantis, Bifidobacterium inopinatum, Bifidobacterium lactis, Bifidobacterium lactentis, Bifidobacterium liberorum, Bifidobacterium longum, Bifidobacterium magnum, Bifidobacterium merycicum, Bifidobacterium minimum, Bifidobacterium mongoliens, Bifidobacterium parvulorum, Bifidobacterium pseudocatenulatum, Bifidobacterium pseudolongum, Bifidobacterium psychraerophilum, Bifidobacterium pullorum, Bifidobacterium ruminale, Bifidobacterium ruminantium, Bifidobacterium saeculare, Bifidobacterium scardovi, Bifidobacterium subtile, Bifidobacterium suis, Bifidobacterium thermacidophillum,* and *Bifidobacterium thermophilum,* and *Bifidobacterium longum* is most preferable.

All of these bacteria are commercially available or can be obtained easily from a depository. For example, *Bifidobacterium longum* ATCC-15707, *Bifidobacterium bifidum* ATCC-11863, *Bifidobacterium infantis* ATCC-15697, etc. can be obtained easily from ATCC (The American Type Culture Collection).

Furthermore, the strain of each bacterium is not particularly limited; examples of strains of *Bifidobacterium longum* include *Bifidobacterium longum* 105-A strain, *Bifidobacterium longum* aE-194b strain, *Bifidobacterium longum* bs-601 strain, and *Bifidobacterium longum* M101-2 strain, and among them *Bifidobacterium longum* 105-A strain is preferable.

Examples of strains of *Bifidobacterium breve* include *Bifidobacterium breve* standard strain (JCM1192), *Bifidobacterium breve* aS-1 strain, and *Bifidobacterium breve* I-53-8W strain, and among them *Bifidobacterium breve* standard strain and *Bifidobacterium breve* aS-1 strain are preferable.

Examples of strains of *Bifidobacterium infantis* include *Bifidobacterium infantis* standard strain (JCM1222) and *Bifidobacterium infantis* I-10-5 strain, and among them *Bifidobacterium infantis* standard strain and *Bifidobacterium infantis* I-10-5 strain are preferable.

Examples of strains of *Bifidobacterium lactentis* include *Bifidobacterium lactentis* standard strain (JCM1220).

Since the gene transfer carrier of the present invention colonizes specifically at the site of an ischemic disease, it is possible to diagnose the site of an ischemic disease by detecting the presence of the gene transfer carrier. Detection of the gene transfer carrier can be carried out simply by for example labeling the gene transfer carrier. From the viewpoint of use in the diagnosis of a disease, it is preferable to carry out detection with low invasiveness, and it is preferable that there is little adverse effect on a delivery target by labeling. Therefore, in a preferred embodiment of the present invention, the gene transfer carrier expresses a fluorescent protein as a protein that is useful for diagnosis. Examples of the fluorescent protein include various types of green fluorescent proteins (GFPs) and red fluorescent proteins (RFPs).

Since the gene transfer carrier of the present invention colonizes specifically at the site of an ischemic disease, a protein that is expressed at the colonization site is inevitably delivered specifically to the site of the ischemic disease. Therefore, making the gene transfer carrier of the present invention express a protein that is used for the treatment of an ischemic disease enables the ischemic disease to be treated effectively. Therefore, in a preferred embodiment of the present invention, the gene transfer carrier expresses a protein that is useful for the treatment of an ischemic disease.

Examples of the protein that is useful for the treatment of an ischemic disease include, but are not limited to, a protein having angiogenesis promoting activity and a protein involved in vasodilation. Examples of proteins having angiogenesis promoting activity include, but are not limited to, fibroblast growth factor (FGF), endothelial cell growth factor (ECGF), vascular endothelium growth factor (VEGF), hepatocyte growth factor (HGF), angiogenic growth factor (AGF), platelet-derived growth factor (PDGF), transforming growth factor β (TGF β), angiopoietin, and ephrin, and examples of factors involved in vasodilation include a prostaglandin. Examples of other proteins that are useful for the treatment include colony stimulating factors such as granulocyte colony stimulating factor (G-CSF) and granulocyte-macrophage colony stimulating factor (GM-CSF), nerve growth factor (NGF), brain-derived neurotrophic factor (BDNF), a neurotrophin such as neurotrophin 3, and insulin-like growth factor (IGF).

With regard to a plasmid that can be used in transformation of the gene transfer carrier of the present invention, any plasmid may be used as long as it functions in the gene transfer carrier bacterium and does not impair the anaerobic properties of the bacterium as described above. However, there is a possibility that, in the body of the delivery target, a plasmid that is used for transformation might be horizontally transferred to another bacterium within the body such as for example *E. coli*, and in this case there is an undeniable risk that the plasmid will replicate in the other bacterium to which it is horizontally transferred, and as a result the protein encoded by the plasmid will be expressed at an unintended site. Therefore, in a preferred embodiment, the transforming plasmid is a non-shuttle plasmid.

In the present specification, the term 'shuttle plasmid' means a plasmid that can replicate in two or more different hosts, and is used interchangeably with the term 'shuttle vector plasmid'. Therefore, the term 'non-shuttle plasmid' means a plasmid that can replicate only in one type of host.

The gene transfer carrier of the present invention produces a protein that is encoded by the transforming plasmid in the bacterial body, and since such a protein exhibits its therapeutic effect only when it is released from the bacterial body, in order to make a protein that is usually not secreted from the bacterial body exhibit a therapeutic effect, it is necessary to destroy the bacterium. In order to solve this problem, in a preferred embodiment the transforming plasmid further comprises a gene sequence coding for a secretory signal peptide.

In the present specification, the term 'secretory signal peptide' means a peptide sequence, present at the terminal of a protein, having the function of secreting a protein produced within the bacterial body from the bacterial body. Examples of secretory signal peptides that can be used include, but are not limited to, amyB of *Bifidobacterium adolescentis*, Sec1, Sec2, and Sec3 of *Bifidobacterium breve*, and peptides encoded by DNA sequences of SEQ ID Nos: 1 to 22.

The gene transfer carrier of the present invention may be for example prepared as described below.

For example, in accordance with a standard method, a gene coding for at least one type of a protein that is useful for the diagnosis or treatment of a desired ischemic disease is inserted into a shuttle plasmid having a replication initiation site that functions in both a transformed bacterium and a bacterium other than the transformed bacterium, for example, *Bifidobacterium* and *E. coli*, thus preparing a shuttle plasmid.

If desired, removing the replication initiation site for the bacterium other than the transformed bacterium from this shuttle plasmid enables a non-shuttle plasmid to be prepared.

Furthermore, if desired, replacing a promoter gene with a secretory signal and its promoter gene functioning in at least *Bifidobacterium*, and replacing a terminator gene with a terminator gene of the secretory signal peptide functioning in *Bifidobacterium* enables a plasmid comprising a gene sequence coding for the secretory signal peptide to be further prepared.

Procedures of each of the above-mentioned steps may be carried out in accordance with a method known in the genetic engineering field.

A given anaerobic bacterium that is to be transformed is subjected to a method known in the genetic engineering field using the above-mentioned transforming plasmid, thus preparing a transformant.

The present invention further relates to a pharmaceutical composition for an ischemic disease containing the above-mentioned gene transfer carrier.

The pharmaceutical composition of the present invention is not particularly limited as long as it contains the gene transfer carrier of the present invention. With regard to the gene transfer carrier of the present invention, at least one type thereof may be contained, and two or more types thereof may be contained. Furthermore, the pharmaceutical composition of the present invention may be used in a combination with a treatment agent for an ischemic disease or a pharmaceutical composition containing a compound, other than the gene transfer carrier of the present invention, exhibiting a therapeutic effect for an ischemic disease.

Furthermore, the pharmaceutical composition of the present invention may contain an optional component in addition to the gene transfer carrier of the present invention as long as it does not impair the effects of the present invention. Examples of such optional components include pharmaceutically acceptable carriers, excipients, and diluents.

The dosage form of the pharmaceutical composition of the present invention is not particularly limited, and examples thereof include a liquid agent or solid preparation containing the gene transfer carrier of the present invention. The liquid agent may be produced by purifying a liquid culture of the anaerobic bacterium of the gene transfer carrier of the present invention, adding thereto as necessary an appropriate physiological saline, supplementary fluid, or pharmaceutical additive, and charging an ampoule or a vial therewith. The solid preparation may be produced by adding an appropriate protecting agent to a liquid agent, charging an ampoule or a vial therewith, and lyophilizing or L-drying it, or adding an appropriate protecting agent to a liquid agent, lyophilizing or L-drying it, and then charging an ampoule or a vial therewith.

As a method for administering the pharmaceutical composition of the present invention, both oral administration and parenteral administration are possible, but parenteral administration is preferable; for example intravenous injection, subcutaneous injection, local infusion, intracerebroventricular administration, etc. may be carried out, and intravenous injection, that is, systemic administration, is most preferable.

The dose of the gene transfer carrier of the pharmaceutical composition of the present invention is not particularly limited as long as it is a sufficient amount that enables growth at a disease site and an effective therapeutic dose of active protein to be expressed, but from the viewpoint of economy and from the viewpoint of side effects being avoided as far as possible, it is preferable to use as small an amount as possible in a range that can give a necessary therapeutic effect.

The dose of the gene transfer carrier of the pharmaceutical composition of the present invention may be appropriately selected according to the extent of a disease and the body weight, age, and sex of a patient, and may be appropriately increased/decreased according to the degree of improvement.

For example, when the pharmaceutical composition of the present invention is used, the dose is set appropriately according to the therapeutic activity for the disease exhibited by the anaerobic bacterium itself that is used, the type of protein, etc. having therapeutic activity for the disease produced by the anaerobic bacterium used, and the amount of the active protein produced by the anaerobic bacterium used.

Specifically, in the case of for example intravenous administration, since it is particularly necessary to reduce a risk such as embolization by a clump of bacteria, it is preferable to inject an injectable preparation having as low a concentration as possible a plurality of times, or continuously infuse a dilution with an appropriate supplementary fluid. For example, in the case of an adult, $10^6$ to $10^{12}$ cfu of the bacterial cells of the anaerobic bacterium of the present invention per kg of body weight is administered once or multiple times a day for 1 day to multiple days continuously or at appropriate intervals. More specifically, 1 to 1000 mL per adult of a preparation containing $10^4$ to $10^{10}$ cfu/mL of bacterial cells of the *Bifidobacterium* of the present invention is administered directly or after dilution with an appropriate supplementary fluid once or multiple times a day for 1 day to multiple days continuously.

Furthermore, in the case of local administration involving direct administration to the diseased tissue, it is desirable to administer a high concentration injection to multiple positions of the diseased tissue because the bacterium is required to colonize and grow in the entire diseased tissue if possible. For example, in the case of an adult, $10^6$ to $10^{12}$ cfu of bacterial cells of the *Bifidobacterium* of the present invention per kg of body weight is administered once or multiple times a day for 1 day to multiple days as necessary, continuously or at appropriate intervals. More specifically, 1 to 1000 mL per adult of a preparation containing $10^4$ to $10^{10}$ cfu/mL of bacterial cells of the *Bifidobacterium* of the present invention is administered directly, multiple times a day, for 1 day to multiple days continuously as necessary.

When it is confirmed that the bacterium in the diseased tissue has disappeared during the treatment period, the treatment is temporarily suspended, and the bacterium is administered again in the same way as described above.

The expression 'being formed by combining X and Y' in the present invention includes both a case in which X and Y are separate configurations and a case in which X and Y are of the same configuration (for example a configuration containing X and Y). When X and Y are separate configurations, a case in which X and Y further contain another component is also included.

The gene transfer carrier of the present invention colonizes and grows specifically at the site of an ischemic disease and does not grow in normal tissue that is not under an anaerobic environment. Therefore, the gene is delivered specifically to a disease site without there being local administration targeted at the site of an ischemic disease. From the viewpoint of ease of administration and low invasiveness, the pharmaceutical composition of the present invention is therefore preferably administered systemically.

One aspect of the present invention includes a method for diagnosing or treating an ischemic disease using the gene transfer carrier formed from the anaerobic bacterium. In accordance with use of the gene transfer carrier of the present invention, it becomes possible to carry out diagnosis or treatment with high efficiency and high safety.

In the method of the present invention, the gene transfer carrier of the present invention is administered to a target having an ischemic disease. As the administration method, both oral administration and parenteral administration are possible, but parenteral administration is preferable; examples thereof include intravenous injection, subcutaneous injection, local infusion, and intracerebroventricular administration, and intravenous injection, that is, systemic administration, is most preferable.

Therefore, in a preferred embodiment of the method of the present invention, the gene transfer carrier of the present invention is systemically administered. Since the gene transfer carrier of the present invention can specifically deliver the gene to the site of an ischemic disease, even when systemic administration such as intravenous injection is carried out without using a catheter or intramuscular injection, it can colonize and grow at the site of an ischemic disease, and exhibit an effect. Therefore, compared with a conventional therapy, a treatment with very low invasiveness becomes possible.

EXAMPLES

The present invention is more specifically explained below through the presentation of selected studies performed to confirm the utility and effectiveness of the invention, however the technical scope of the present invention is not limited to these examples.

Example 1: Mouse Lower Limb Ischemia Model Experiment

In order to verify the ability of the gene transfer carrier of the present invention to deliver specifically to the site of an ischemic disease, a mouse model with lower limb ischemia was prepared, and examination was carried out by administering the gene transfer carrier of the present invention.

(1) Preparation of Model

As a test animal, an 8-9 week-old male C57BL/6 mouse (acquired from Charles River Laboratories Japan, Inc.) was used, and a lower limb ischemia model mouse (ischemic model) was prepared by the procedure below. For anesthesia, 0.3 mL of 3.6% chloral hydrate (acquired from Nacalai Tesque, Inc.) was intraperitoneally injected. After the abdomen and the lower limb were shaved, a section from the common femoral artery to the popliteal artery was ligated using 7-0 polypropylene thread, and the femoral artery was excised. After the interior of the wound was washed with physiological saline, the wound was sutured using 5-0 nylon thread.

(2) Blood Flow Measurement by Laser Doppler Blood Flow Meter

After the mouse was anesthetized, blood flow was measured using a laser Doppler blood flow meter (Moor Instruments) before lower limb muscle removal mentioned in (3). Blood flow was measured from the lower limb to the digit tip on both sides, and expressed as an ischemic side/non-ischemic side ratio. The blood flow measurement was carried out immediately before the model was prepared, immediately thereafter, and 1, 2, 3, 4, 5, 7, 10, 14, 21, and 28 days thereafter.

Figure 1A:
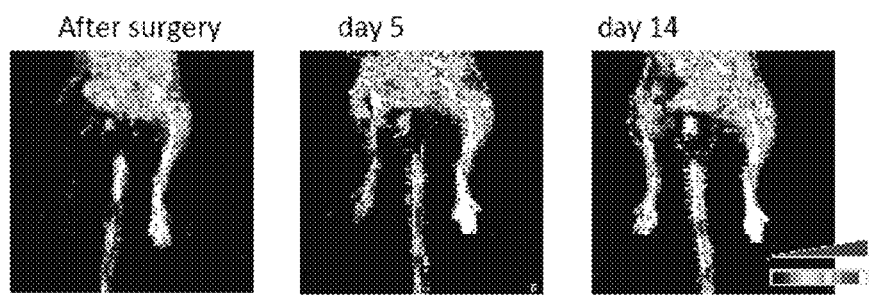
FIG. 1A shows images of measurement by a laser Doppler blood flow meter of a lower limb ischemia model mouse (ischemic model).
Figure 1B:
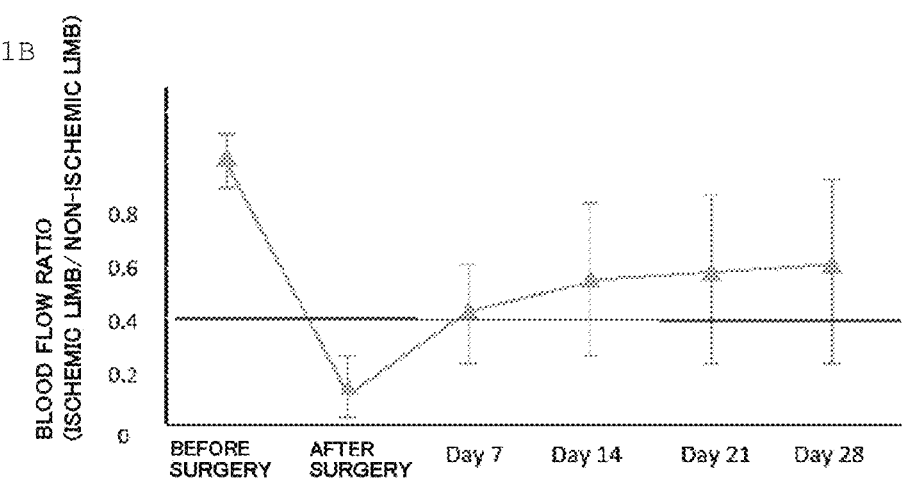
FIG. 1B shows a graph showing change in blood flow ratio (ischemic limb/non-ischemic limb).
Figure 2:
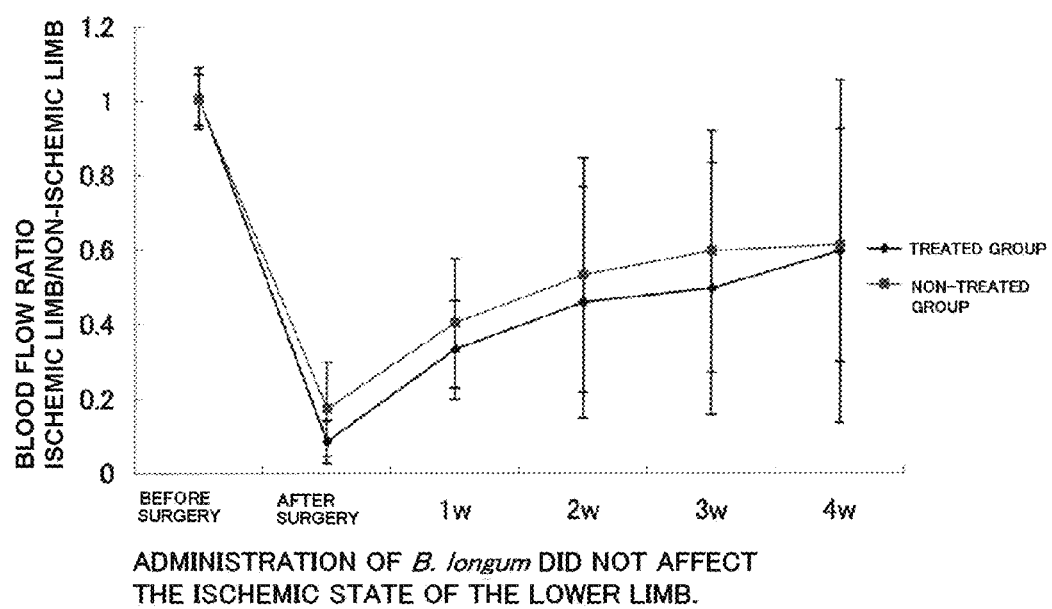
FIG. 2 is a graph comparing the change in blood flow ratio between the group that was treated with *B. longum* of the present invention and the group that was not treated in the ischemic model. There was no significant difference in the change in blood flow ratio between the treated group and the non-treated group.
Figure 3:
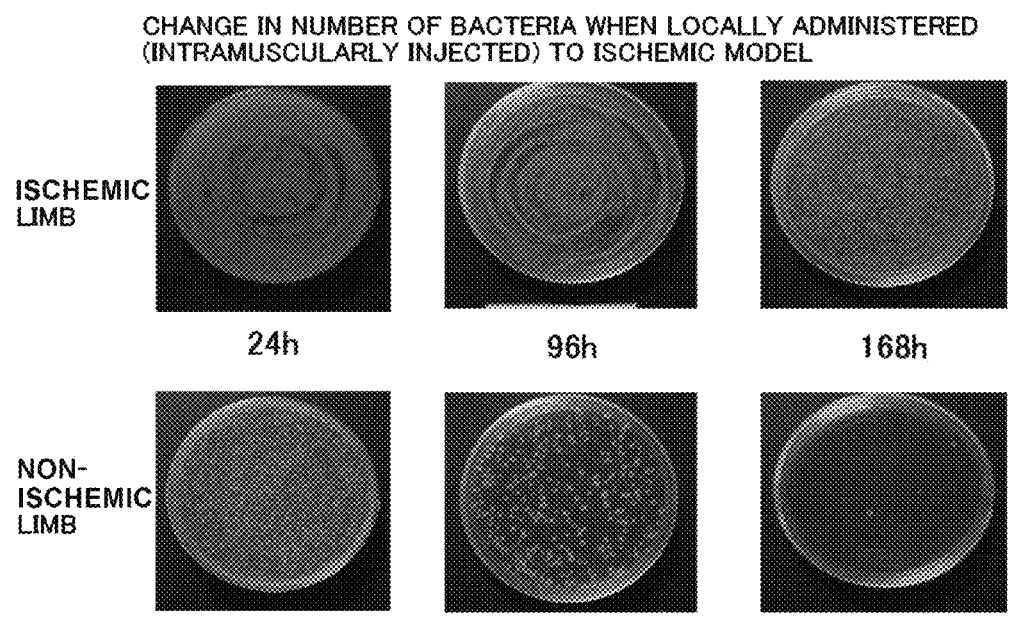
FIG. 3 shows photographs of detected *B. longum* of the present invention existing in samples collected from an ischemic limb and a non-ischemic limb of the ischemic model local administration group. In the ischemic limb, a large number of bacteria were observed even at 168 hours after administration, but in the non-ischemic limb almost none were observed.

The results are shown in FIGS. 1 and 2. In such a lower limb ischemia model, after the surgery the blood flow rate of the ischemic limb became no greater than 20% of that of the non-ischemic limb; it recovered up to about 40% 1 week after the surgery, and it recovered up to about 60% 4 weeks after the surgery (FIG. 1). Change in blood flow was compared between a group to which B. longum was administered and a group to which nothing was administered (FIG. 3). There was no significant difference in change in blood flow between the treated group and the non-treated group after surgery (FIG. 2), and it was found that the presence of B. longum did not affect the ischemic state.

(3) Administration and Detection of B. Longum

B. longum that had been transformed by a pBLES100 plasmid and turned into a spectinomycin resistant bacterium was subcultured twice in MRS medium (acquired from Kanto Kagaku). The liquid culture obtained by subculturing twice was subjected to centrifugation using physiological saline and used as a suspension in physiological saline. As a local administration model, immediately after a lower limb ischemia model was prepared, $1 \times 10^9$ cfu/mL$\times$0.1 mL$\times$2 positions of B. longum was administered to each of the ischemic limb and the non-ischemic limb by intramuscular injection. As a systemic administration model, 0.2 mL of $1 \times 10^9$ cfu/mL B. longum was administered to the tail vein. 1, 2, 3, 4, 5, 7, 10, and 14 days after the bacterium was administered, the left and right lower limb muscles were removed from each of the administration models (n=5 for each). After the tissue was homogenized, it was smeared on a BL plate and cultured at 37° C. under anaerobic conditions for 3 days. After culturing, the number of colonies on each plate was measured to obtain bacterial counts for the ischemic limb and the non-ischemic limb.

Figure 4:
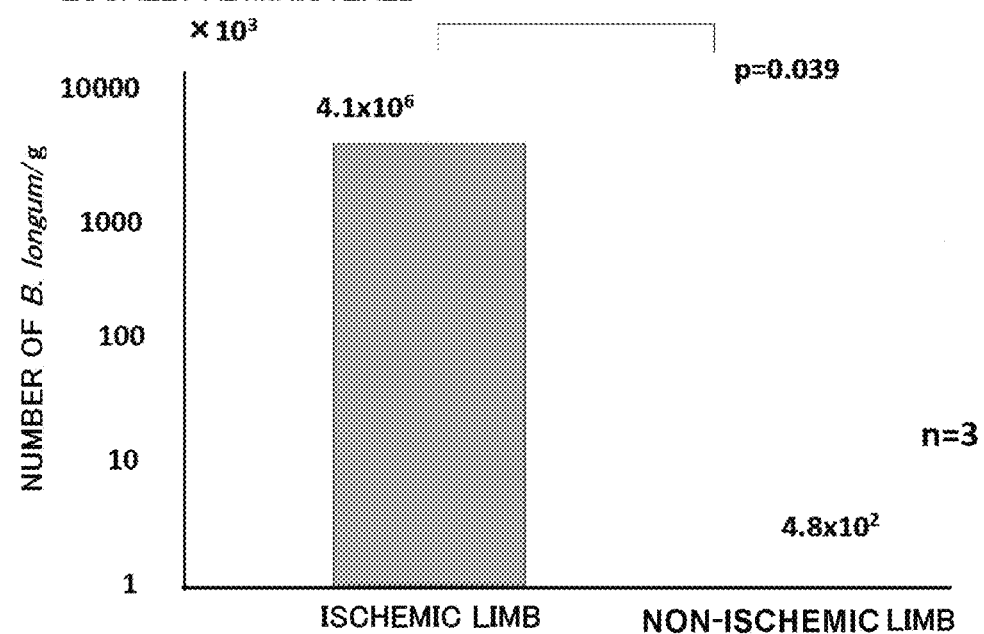
FIG. 4 is a graph of bacterial count in the ischemic limb and the non-ischemic limb at 168 hours after administration to the ischemic model local administration group.

The results are shown in FIGS. 3 through 6. In the case of local administration, accumulation of a larger number of bacteria in the ischemic limb than in the non-ischemic limb was observed at 24 hours after surgery. In the non-ischemic limb, the bacterial count decreased with time thereafter, and almost no bacteria were observed at 168 hours after surgery. This contrasted strongly with the large number of bacteria observed in the ischemic limb at 168 hours. The bacterial count per g of muscle tissue at 168 hours after surgery was $4.8 \times 10^2$ for the non-ischemic limb whereas it was $4.1 \times 10^6$ for the ischemic limb, there thus being a significant difference (p=0.039, n=3) (FIGS. 3 and 4).

Figure 5:
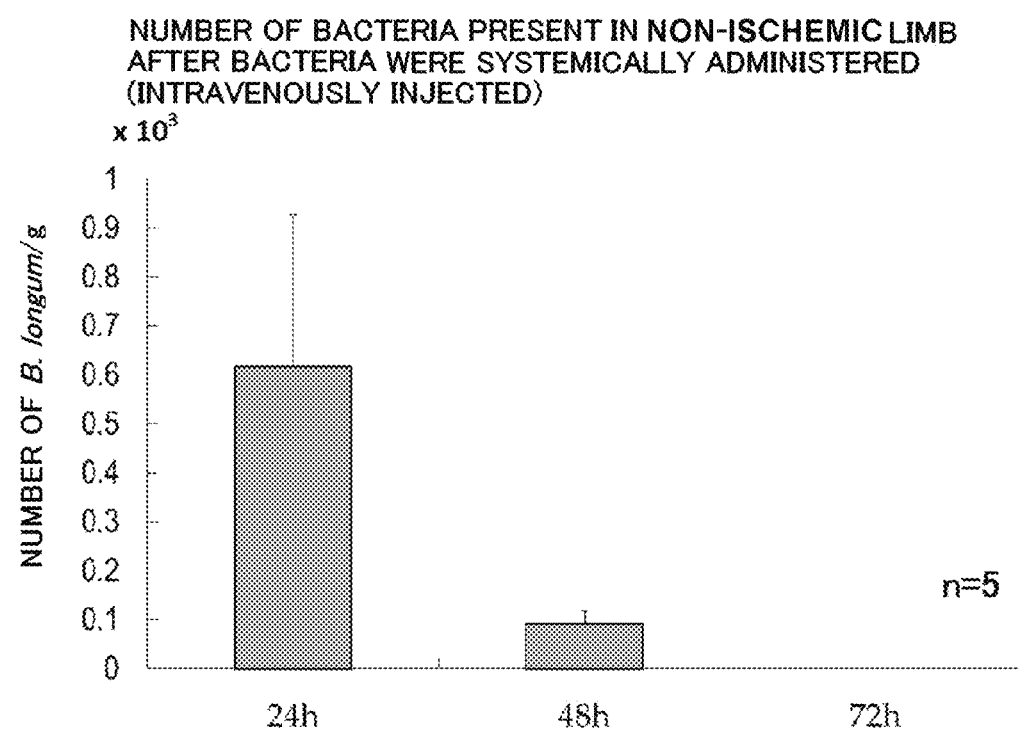
FIG. 5 is a graph of the change in *B. longum* count at 24 hours, 48 hours and 72 hours in the non-ischemic limb of the ischemic model systemic administration group. Even in the systemic administration group almost no bacteria were observed at 48 hours, and none were observed at 72 hours.
Figure 6:
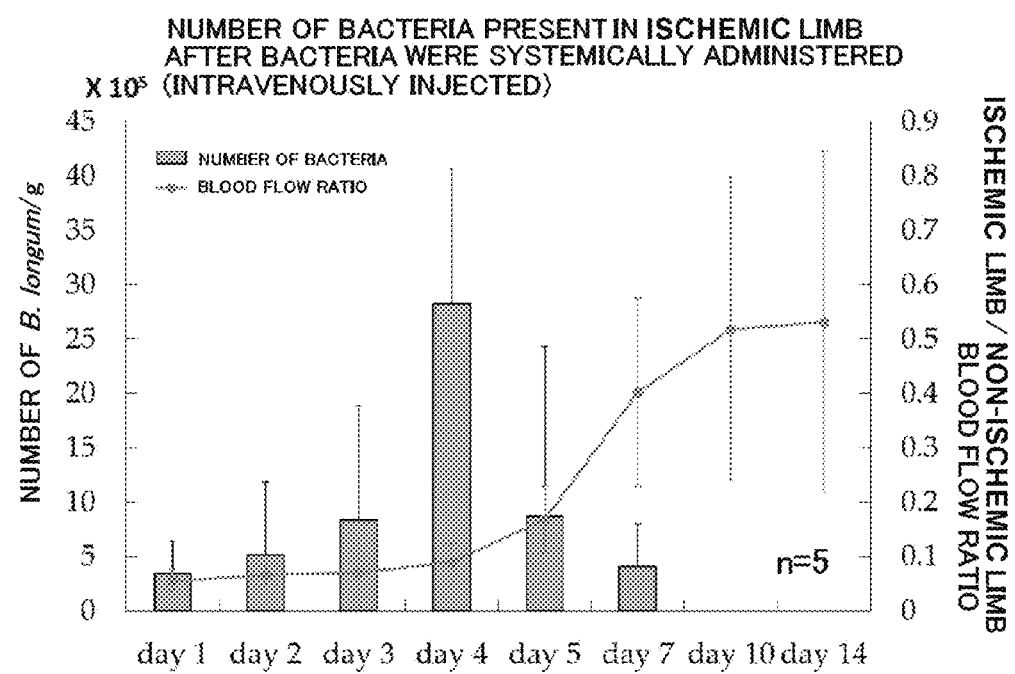
FIG. 6 is a graph of change in blood flow ratio and change in bacterial count with respect to time in the ischemic limb of the ischemic model systemic administration group. It can be seen that the bacterial count increased with time after administration, and the bacterial count decreased as the blood flow to the ischemic site recovered.
Figure 7:
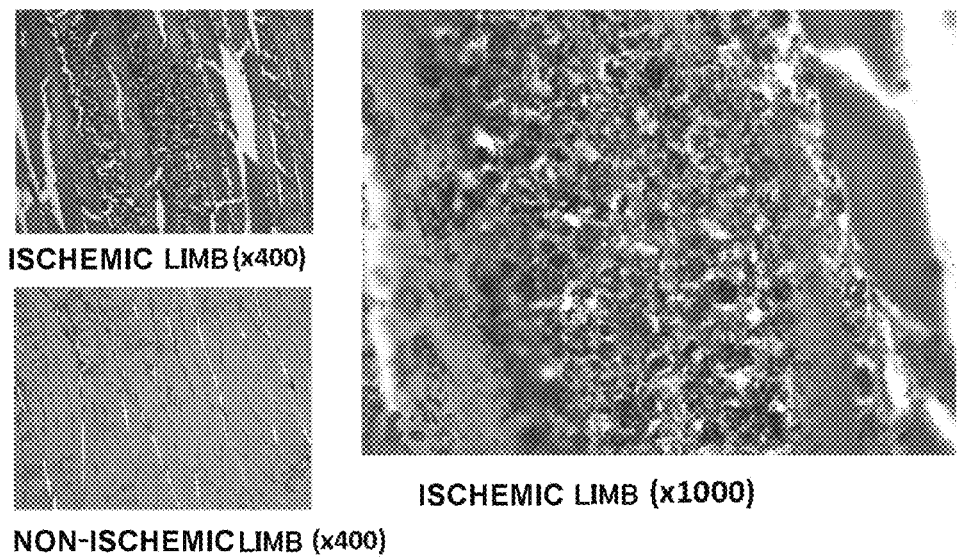
FIG. 7 shows Gram stain images of muscle tissue at 4 days after administration in the ischemic model systemic administration group. Whereas no Gram-stained bacteria were observed in the non-ischemic limb, many Gram-stained bacteria were observed in the ischemic limb.

Similar results were obtained for the case of systemic administration. That is, in the non-ischemic limb about $0.6 \times 10^3$ bacteria were observed at 24 hours after surgery, decreasing to about $0.1 \times 10^3$ at 48 hours; none were observed at 72 hours after surgery. Conversely, in the ischemic limb about $3.5 \times 10^5$ bacteria were observed 24 hours after surgery with the number increasing over time to a maximum of about $2.7 \times 10^6$ at 4 days after surgery. Subsequently the bacterial count decreased as the blood flow recovered, and none were observed 10 days after surgery (FIGS. 5 and 6). In the case of systemic administration, it was found that it took longer for the bacteria to colonize compared to local administration, but they specifically colonized the site of the ischemic disease, even with intravenous administration. Since the maximum value for the bacterial count was observed on the 4$^{th}$ day, when the blood flow ratio was the lowest, and henceforth decreased as the blood flow ratio improved, the possibility that *B. longum* grows according to the degree of ischemia is suggested.

(4) Histological Analysis

The lower limb muscle was removed 96 hours after *B. longum* was administered to the mouse in the same way as in (3). The lower limb muscle was immersed in a 20% neutral formalin buffer for 48 hours to fix the tissue. After that, it was embedded in paraffin to form a paraffin block. Paraffin tissue section slides were prepared by slicing the paraffin block into 3 μm sections, which were placed on slide glass, and air dried at 44° C. for 24 hours. After deparaffinization, Gram staining was carried out using a neo-B & M Wako Gram staining solution (Wako Pure Chemical Industries, Ltd.). After staining, observation using an optical microscope was carried out.

The results are shown in FIG. 6. In the non-ischemic limb no Gram stained bacteria were detected, but in the ischemic limb Gram stained bacteria were observed, and it was confirmed that there was colonization by the administered *B. longum*.

Example 2: Mouse Lower Limb Necrosis Model Test (1) Preparation of Model

It was suggested in Example 1 that the colonizing *B. longum* count decreased as the blood flow recovered, and in order to confirm this a lower limb necrosis model (necrotic model) mouse with a more serious degree of ischemia was prepared. As a test animal, a 6-7 week-old male BALB/c mouse (acquired from Charles River Laboratories Japan, Inc.) was used. As anesthesia, 0.3 mL of 3.6% chloral hydrate (Nacalai Tesque) was intraperitoneally injected. After the abdomen and the lower limb were shaved, a section from the common femoral artery to the superficial femoral artery was ligated using 7-0 polypropylene thread, and the femoral artery was excised. After the interior of the wound was washed with physiological saline, the wound was sutured using 5-0 nylon thread.

(2) Blood Flow Measurement by Laser Doppler Blood Flow Meter

Figure 8:
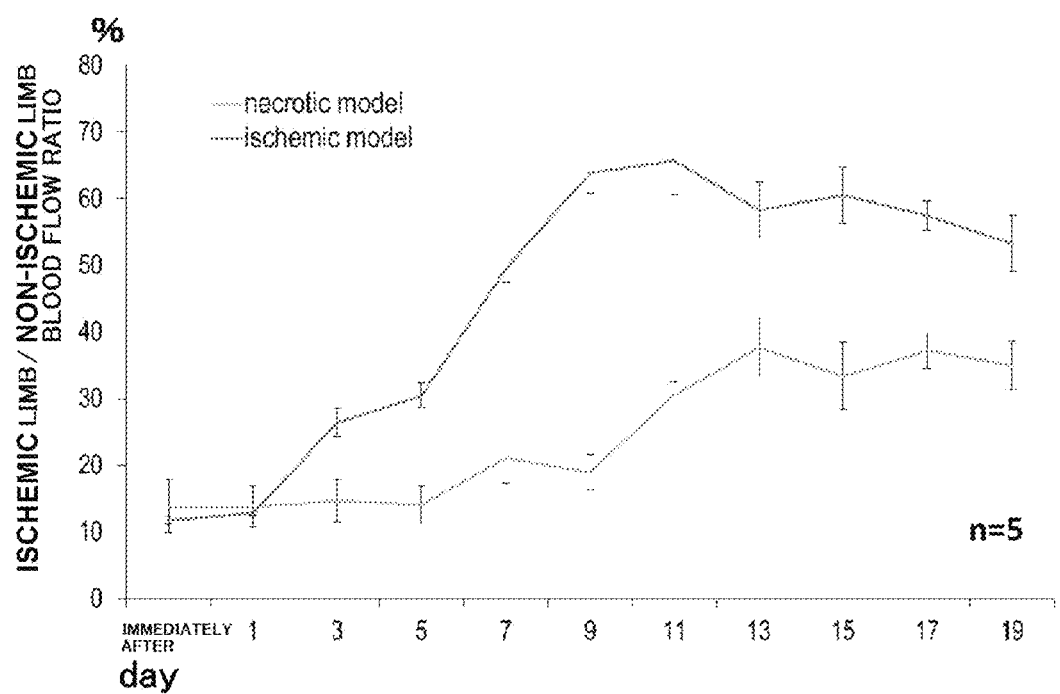
FIG. 8 is a graph of change over time of ischemic limb/non-ischemic limb blood flow ratio of the lower limb ischemia model mouse (ischemic model) and the lower limb necrosis model mouse (necrotic model). It can be seen that in the necrotic model the ischemic state was of longer duration and the degree of recovery was low.

Blood flow was measured in the same way as in Example 1; the results are shown in FIG. 8. It was found that compared with the ischemic model the timing of recovery of the blood flow was slow for the necrotic model, with the final blood flow rate being about 30% of that of the non-ischemic limb. The level of recovery was about half that of the ischemic model, for which the blood flow recovered to about 60%.

(3) Administration and Detection of *B. Longum*

Figure 9:
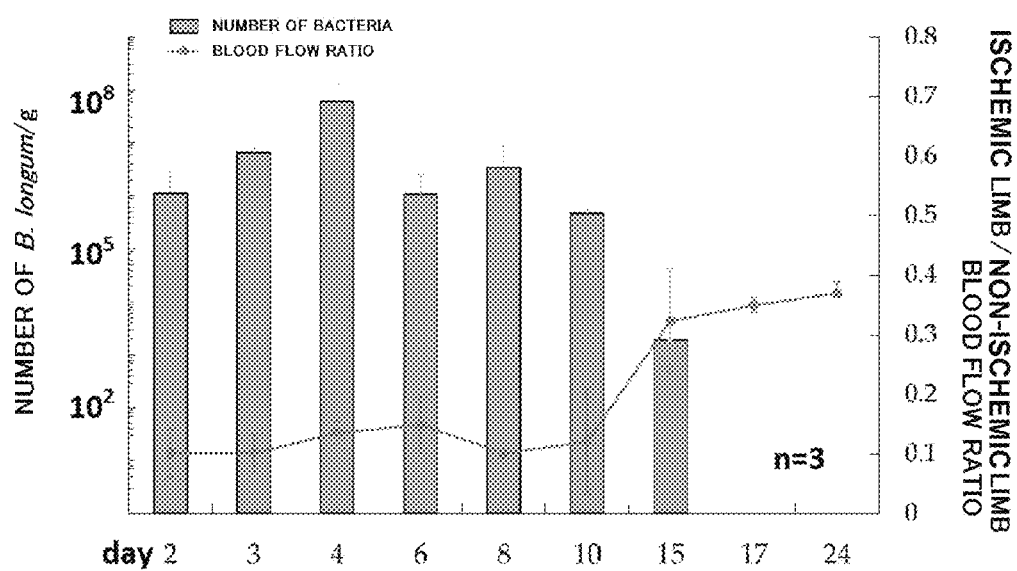
FIG. 9 is a graph of change in blood flow ratio and change in bacterial count with respect to time in the ischemic limb of the necrotic model systemic administration group. It can be seen that the bacterial count increased with time after administration, *B. longum* colonized and grew while the ischemic state continued, and the bacterial count decreased as the blood flow to the ischemic site recovered.
Figure 10:
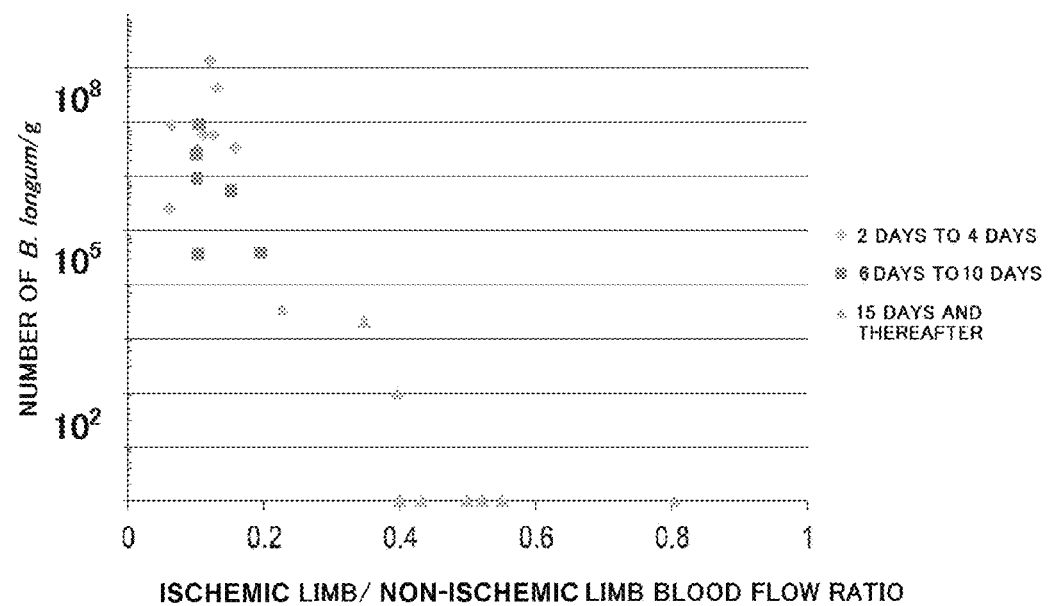
FIG. 10 is a dot diagram of *B. longum* bacterial count plotted with respect to ischemic limb/non-ischemic limb blood flow ratio in the ischemic limb of the necrotic model systemic administration group. It can be seen that the bacterial count decreased as the blood flow ratio increased.

In the same way as in Example 1, *B. longum* was systemically administered, and the muscle tissue of the non-ischemic limb and the ischemic limb was examined. The results are shown in FIGS. 9 and 10. It was found that compared with the ischemic model, *B. longum* was present in the ischemic limb of the necrotic model for a longer period of time. In the same manner as in the ischemic model, the bacterial count decreased as the blood flow recovered, and no bacteria were observed when the blood flow recovered to some degree. From the above results it was found that, regardless of the duration of the time period, *B. longum* colonized and grew in the ischemic limb as long as the ischemic state continued, and the bacterial count started to decrease as the blood flow recovered (that is, recovery from the ischemic state). Therefore, it can be expected that *B. longum* will be delivered specifically to tissue in an ischemic state, express a gene that has been introduced, have the property of disappearing as the ischemic state recovers, and exhibit excellent effects in the diagnosis and treatment of an ischemic disease.

Example 3: Safety Test

The above-mentioned lower limb ischemia model (ischemic model) mouse and the lower limb necrosis model (necrotic model) mouse were both subjected to a safety test. 2, 3, 4, 6, and 7 days after the bacteria were administered, the kidney, liver, spleen, and heart were removed from each administration model (n=3 for each). In addition to these organs, in the ischemic model, the lung was removed, and in the necrotic model the blood was removed. After the tissue was homogenized, it was smeared on a BL plate and cultured at 37° C. under anaerobic conditions for 3 days. After culturing, the number of colonies on each plate was counted to obtain a bacterial count for each tissue.

Figure 11:
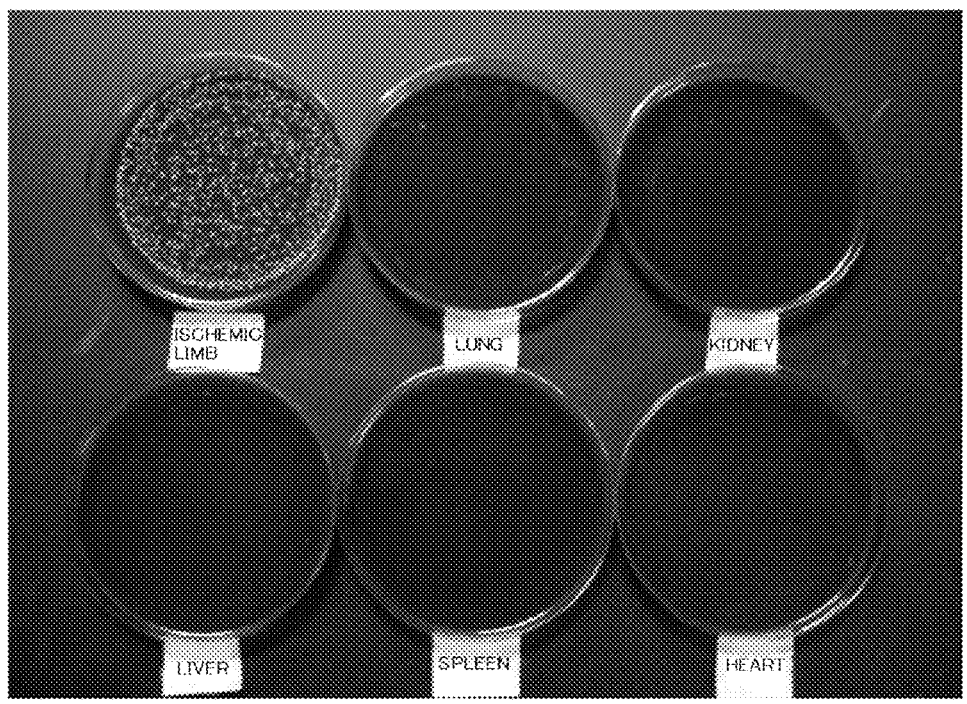
FIG. 11 is a photograph of the results of a *B. longum* detection test in the ischemic limb, the lung, the kidney, the liver, the spleen, and the heart of the ischemic model systemic administration group. Upper left is ischemic limb, upper middle is lung, upper right is kidney, lower left is liver, lower middle is spleen, and lower left is heart. Even with systemic administration, the administered *B. longum* was not observed in organs other than the ischemic limb, which was the ischemic disease site.
Figure 12:
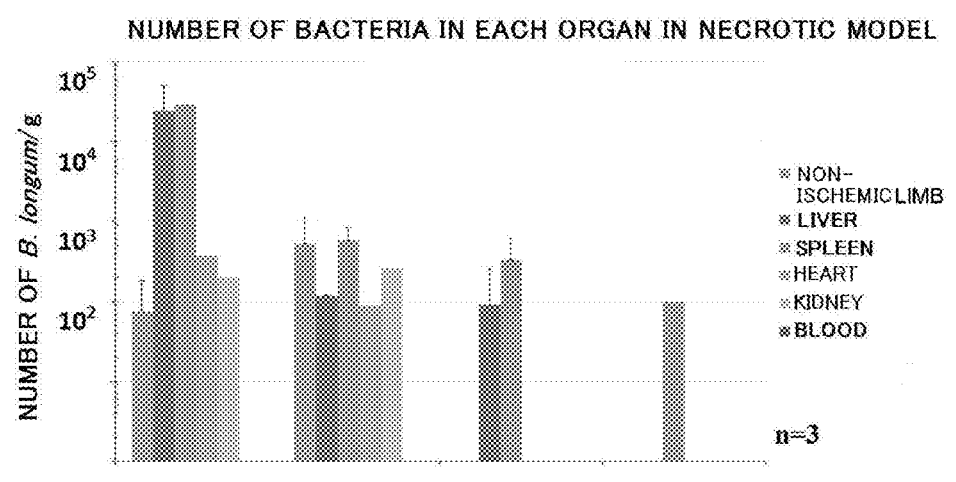
FIG. 12 is a graph of *B. longum* bacterial count with time elapsed in the non-ischemic limb, the blood, the kidney, the liver, the spleen, and the heart of the necrotic model systemic administration group. It can be seen that some bacteria were observed immediately after administration, but they quickly disappeared thereafter. Bacteria were not detected in the blood.

The results are shown in FIGS. 11 and 12. For the ischemic model, *B. longum* was not observed in any of the organs other than the ischemic limb 168 hours after systemic administration. For the necrotic model also, *B. longum* was observed in each organ of the whole body up to 3 days after systemic administration, but it was not observed in organs other than the spleen after 6 days. Furthermore, comparing the treated group and the non-treated group, there was no significant difference in terms of ulceration rate and abscess formation rate of the lower limb, and *B. longum* was not isolated preponderantly from an abscess. From the results above it was found that *B. longum* quickly disappeared from healthy organs and did not have an adverse effect on the disease, such as aggravation of the ischemic state itself or complications.

Example 4: Miniature Swine Myocardial Infarction Model Test

As another representative ischemic disease, an ischemic heart disease such as myocardial infarction can be cited, and in recent years an angiogenic treatment, in particular an angiogenic treatment by means of gene transfer, has been attempted for an ischemic heart disease. However, the same problems as those experienced with other ischemic diseases are seen with the treatment of an ischemic heart disease. In an ischemic heart disease in particular, as a local administration method, a very highly invasive method such as arterial injection using a coronary artery catheter, local injection using a coronary artery catheter, or open chest intramyocardial injection is required, and although angiogenic therapy is thought to be beneficial to a target that cannot receive another therapy such as percutaneous coronary intervention (PCI) or a coronary artery bypass graft (CABG) in particular, at the present it is mainly used in combination with other therapies.

In order to confirm that the gene transfer carrier of the present invention functions effectively in myocardial infarction, a test was carried out as follows.

(1) Preparation of Model

As a test animal, a male Gottingen miniature swine (15 kg) (acquired from Chugai Research Institute for Medical Science) was used. 15 mg/kg of Ketaral (acquired from Sankyo) and atropine sulfate (acquired from Tanabeseiyaku) (25 mg) were intramuscularly injected, and an anesthetic state was maintained by an inhalation anesthetic FLO-THENE (acquired from Takeda Chemical Industries, Ltd.) (2% to 5%). After the chest was opened, the left anterior descending coronary artery was ligated using 3-0 silk thread. During the surgery, 2% Xylocaine (acquired from AstraZeneca) (1 mL to 2 mL) was administered. Before closing the chest, the interior of the pericardium was washed with 100 mL of Lactec (acquired from Otsuka Pharmaceutical Co., Ltd.).

(2) Histological Analysis

In order to confirm myocardial infarction, triphenyltetrazolium chloride (TTC) staining, hematoxylin/eosin (HE) staining, and Masson trichrome (MT) staining were carried out. In TTC staining, the heart removed 7 days after preparing the myocardial infarction model was sliced into a thickness of 5 mm and incubated in 1% TTC solution (acquired from SIGMA) at 37° C. for 5 minutes. After that, examination was carried out with the naked eye.

In hematoxylin/eosin (HE) staining, after deparaffinization, staining was carried out using hematoxylin for 30 seconds to 1 minute, washing was carried out using running water for 10 minutes, and staining was then carried out with a 0.5% eosin solution for 30 seconds. After staining, dehydration, clearing, and embedding were performed; examination was carried out using an optical microscope.

In Masson's trichrome (MT) staining, each section was Bouin-fixed and then washed with running water for 10 minutes. After washing, the samples were immersed in a mixed solution of equal parts 10% potassium dichromate and 10% trichloroacetic acid for 10 minutes, then immersed in an iron hematoxylin stain solution for 5 minutes, and washed with running water for 5 min. After washing the samples were immersed in a Ponceau/acid fuchsin/azophloxine solution for 1 minute, and then immersed in a 2.5% phosphotungstic acid solution for 10 minutes. Next, the sections were immersed in a 2% orange G solution for 5 minutes and washed with a 1% aqueous solution of acetic acid, stained in a Light Green solution for 3 minutes, and then washed with a 1% aqueous solution of acetic acid. Dehydration, clearing, and embedding were carried out by the same process as in HE staining.

Figure 14:
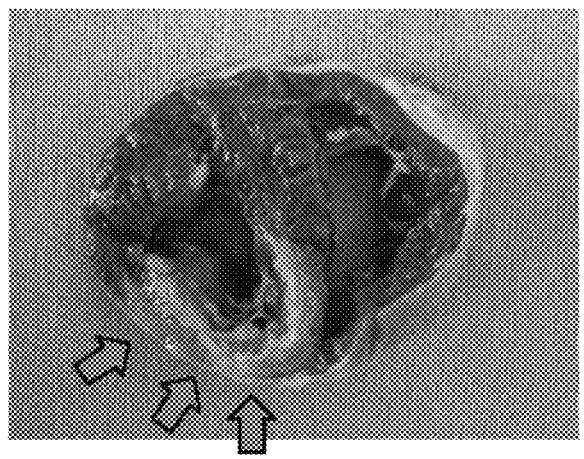
FIG. 14 shows stain images of the heart of the miniature swine myocardial infarction model. a) is a TTC stain image, in which the infarction site (indicated by arrows) was not stained, showing that it is an infarction site. b) and c) are an MT stain image and an HE stain image at the normal myocardial site and the infarction site, respectively. In both of the stain images, depletion of myocardial cells and progression of fibrosis were observed at the infarction site.
Figure 14:
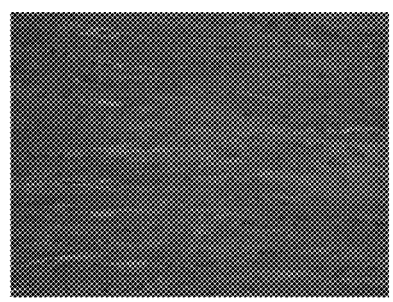
Figure 14:
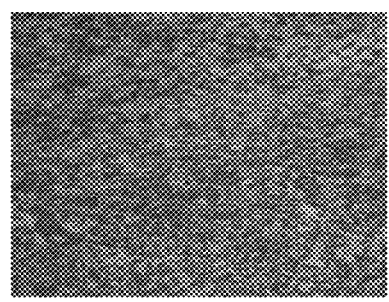
Figure 14:
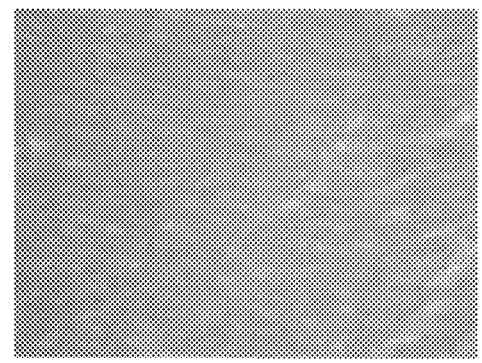
Figure 14:
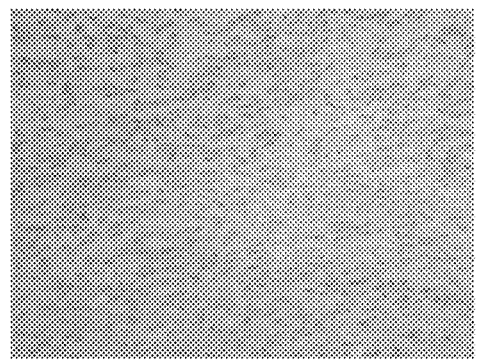

The results are given in FIG. 14. In TTC staining, a transmural infarction site was observed in the left ventricular anterior wall and a part of the interventricular septum closer to the anterior wall. Furthermore, in MT and HE staining, myocardial cell depletion and collagen fiber hyperplasia were observed at the same site, and it was confirmed that the myocardial infarction was complete.

(3) Administration and Detection of *B. Longum*

Figure 13:
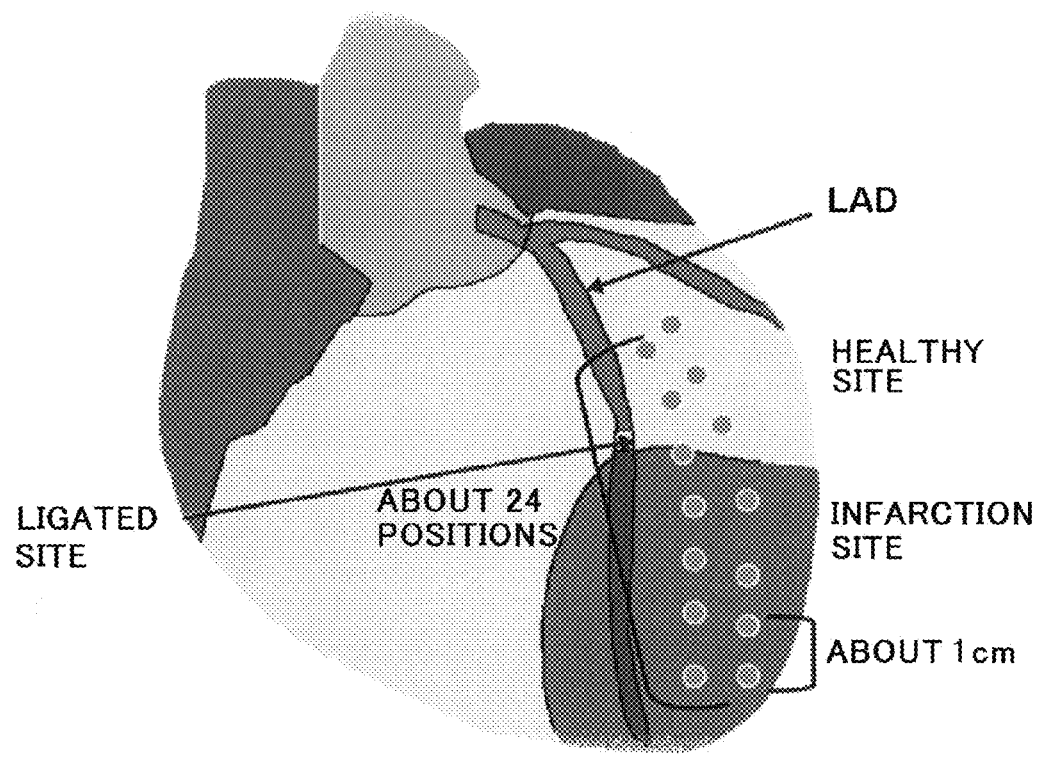
FIG. 13 is a schematic diagram showing the ligation site and the location of bacterial administration of the myocardial infarction model.

*B. longum* was prepared in the same way as in Example 1; immediately after the myocardial infarction model was prepared 0.1 mL of *B. longum* was intramyocardially administered at a concentration of $1 \times 10^9$ cfu/mL to the healthy site and the infarction site at equal intervals of 1 cm (FIG. 13). 4 days and 7 days after the bacteria were administered (n=2 for each) the heart was removed and separated into the infarction site and the healthy site, homogenized, then smeared on a BL plate, and cultured at 37° C. under anaerobic conditions for 3 days. After culturing, the number of colonies on each plate was counted to obtain a bacterial count for the infarction site and the healthy site.

Figure 15:
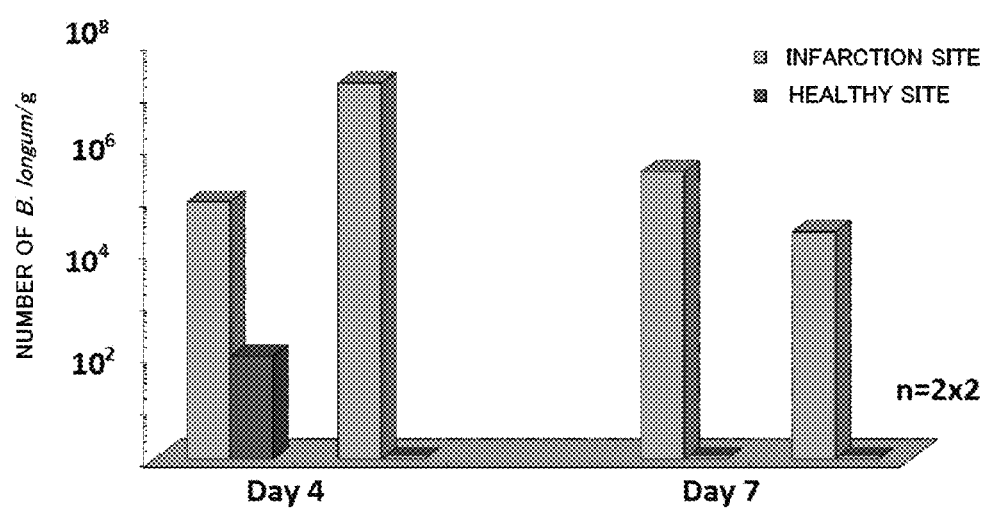
FIG. 15 is a graph showing *B. longum* bacterial count at the infarction site and the healthy site at 4 days and 7 days after administration of *B. longum* in the myocardial infarction model. At 4 days after administration a few bacteria were also observed at the healthy site, but at day 7 bacteria were observed only at the infarction site.

The results are shown in FIG. 15. On the 4$^{th}$ day after administration, few bacteria were observed at the healthy site, but significant bacteria were observed at the infarction site. On the 7$^{th}$ day after administration, no bacteria were detected at the healthy site, and bacteria were observed only at the infarction site. It can be seen from the above that in myocardial infarction also *B. longum* colonized and grew specifically at the infarction site.

Example 5: Constructing a Non-Shuttle hFGF2-Expressing Plasmid for *Bifidobacterium*

(1) Construction of an Expression Plasmid Vector p37.

A plasmid pCDshuttle (International application No: 2009/128272) was used as template for performing PCR using primers CDvecF3 (SEQ ID No: 23) and pUCoriR5 (SEQ ID No: 24) to give a PCR product which was used as a vector. The PCR product amplified from the genomic DNA of *Bifidobacterium longum* 105A as template with primers Pins37F (SEQ ID No: 25) and Pins37R (SEQ ID No: 26) was used as an insert. PCR was performed in a conventional manner.

The vector and the insert described as above were ligated using the In-Fusion HD Cloning Kit and the Cloning Enhancer (TAKARA BIO, Inc.); this reaction is hereinbelow mentioned as an "In-fusion reaction". A portion of the reaction solution was used for transforming *E. coli* TOP10 chemically competent cell (Life Technologies Japan Ltd.). The details were according to the product instruction. Transformed *E. coli* was spread onto an LB agar medium (containing 75 µg/mL spectinomycin), statically cultured overnight at 37° C.

Well isolated colonies on the plate as above were picked up, cultured shaken in LB liquid medium (containing 75 µg/mL spectinomycin) overnight at 37° C., from which the plasmid DNA was extracted using the QIAprep Spin Miniprep Kit (QIAGEN). A full-length sequence analysis was carried out for this plasmid DNA to confirm the sequence thereof. The complete plasmid was named p37 (SEQ ID No: 39).

(2) Construction of hFGF2-Expressing Plasmid (Non-Secretory).

Figure 16:
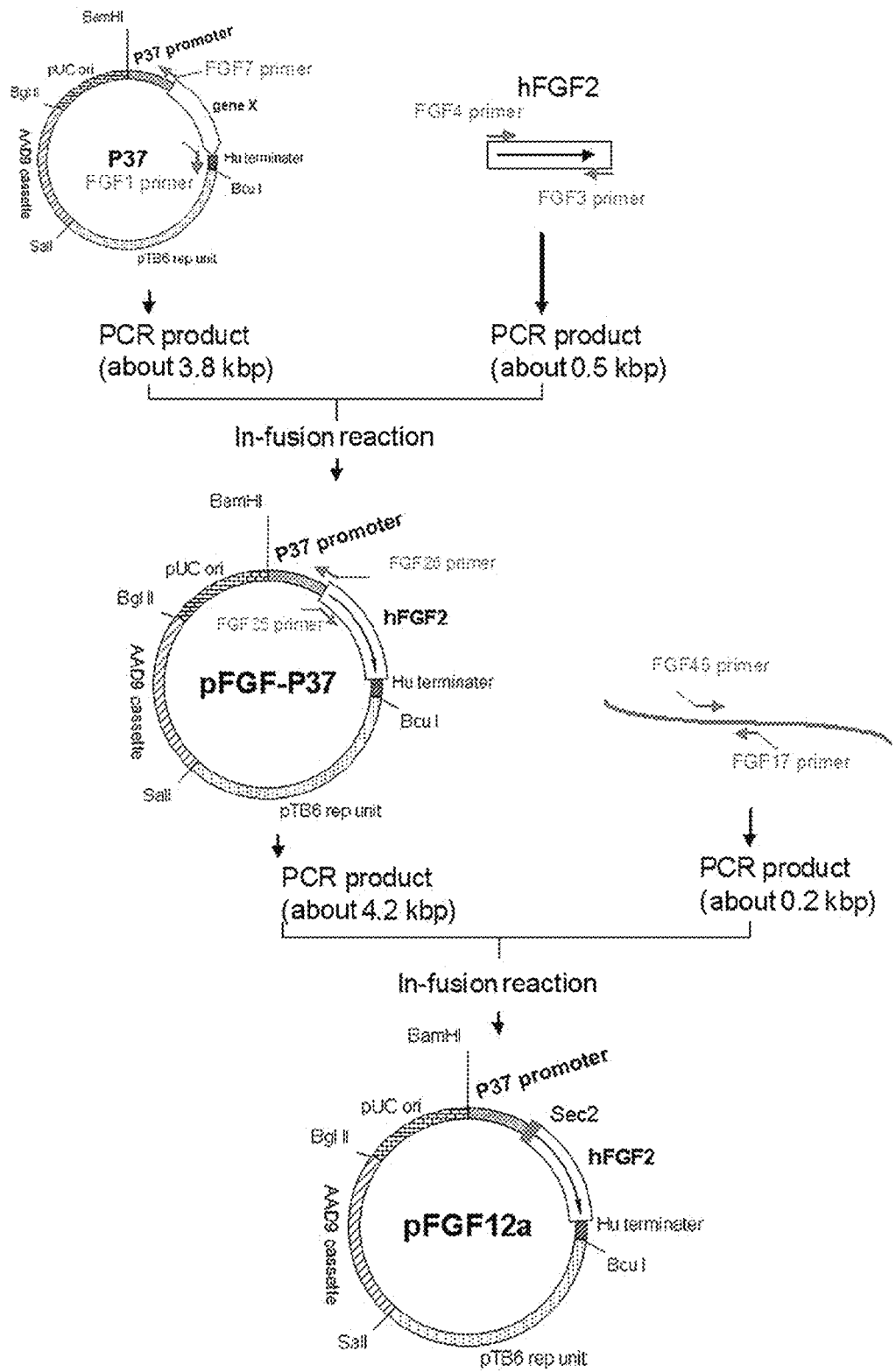
FIG. 16 is a diagram showing a scheme for constructing pFGF12a, which is one embodiment of the transforming plasmid that transforms the gene transfer carrier of the present invention.

FIG. 16 shows a summary of constructing the human FGF2-expressing (non-secretory) plasmid pFGF-P37. The vector was prepared as follows: the plasmid p37 was used as template for performing PCR with primers FGF1 (SEQ ID No: 27) and FGF7 (SEQ ID No: 28), amplifying a DNA of approximately 3.8 kbp consisting of P37 promoter (SEQ ID No: 29), Hu terminator, pTB6 replicon (plasmid replicon in *Bifidobacterium*), AAD9 cassette (spectinomycin resistance gene expression unit) and pUCori moiety (plasmid replication origin in *E. coli*) as the vector. Primers were designed so that the terminal 15 bps of the vector had the same sequence as the terminal 15 bps of the insert shown below. DNA amplification employed the PrimeSTAR HS (Premix) (TAKARA BIO, Inc.), and the PCR conditions were in accordance with the product instruction of the enzyme.

The insert was prepared as follows: based on the amino acid sequence of hFGF2 (a protein of approximately 18 kDa whose translation being started from AUG of GenBank Accession No. #NM_002006), a DNA having codons optimized for *Bifidobacterium* was artificially synthesized (customized by GenScript). Here, the DNA was designed so that a histidine-tag was fused to the C-terminal of the coded hFGF2 protein (SEQ ID No: 30). Using this synthetic DNA as template, PCR amplification with primers FGF3 (SEQ ID No: 31) and FGF4 (SEQ ID No: 32) was carried out in a similar manner as above, amplifying a DNA product of approximately 0.5 kbp as the insert.

The vector and insert as above were ligated by an In-fusion reaction. The details were in accordance with the product instruction. The In-fusion reaction solution was appropriately diluted with 0.1×TE, of which 2 μL was used for transforming *E. coli* TOP10 chemically competent cell (Life Technologies Japan Ltd.). The details were in accordance with the product instruction. Transformed *E. coli* was spread onto an LB agar medium (containing 75 μg/mL spectinomycin), statically cultured overnight at 37° C.

Well isolated colonies on the plate as above were picked up, cultured shaken in LB liquid medium (containing 75 μg/mL spectinomycin) overnight at 37° C., from which the plasmid DNA was extracted using the QIAprep Spin Miniprep Kit (QIAGEN). A part of the plasmid was used for confirming DNA sequence of the hFGF2 expression unit. Sequencing reaction was carried out using the BigDye Terminator v3.1 Cycle Sequencing Kit (Life Technologies Japan Ltd.) and the details were in accordance with the product instruction. Electrophoresis of the sequencing reaction solution was ordered to the Divisions of Instrumental Analysis, Research Center for Human and Environmental Sciences, Shinshu University. Data analysis was carried out using Genetyx Ver. 10. The complete plasmid was named pFGF-P37 (SEQ ID No: 33).

(3) Construction of Secretory hFGF2 Expression Plasmid.

FIG. 16 shows a summary of constructing the human FGF2-expressing (secretory) plasmid pFGF12a. The above-mentioned plasmid pFGF-P37 was used as template for performing PCR with primers FGF35 (SEQ ID No: 34) and FGF26 (SEQ ID No: 35), amplifying a DNA product of approximately 4.2 kbp as the vector. Meanwhile, using the genomic DNA of *Bifidobacterium longum* 105A strain as template, a PCR was performed with primers FGF45 (SEQ ID No: 36) and FGF17 (SEQ ID No: 37), amplifying a DNA product of approximately 0.2 kbp as the insert. The insert comprises a secretory signal and well-conserved N-terminal sequence of Sec2 of *B. breve* UCC2003 (See, Shkoporov A N et. al., Biotechnol Lett (2008) 30: 1983-1988). Amplification of the vector and insert was carried out using PrimeSTAR HS (Premix) (TAKARA BIO, Inc.), where the PCR conditions were in accordance with the product instruction of the enzyme.

The vector and insert as above were ligated by In-fusion reaction, used for transforming *E. coli* TOP10 in a similar manner to that in constructing above-mentioned FGF expression plasmid (non-secretory), and the DNA sequence of hFGF2 expression unit part of the plasmid was confirmed to give a complete plasmid named pFGF12a (SEQ ID No: 38). The constitution of the hFGF2 expression unit part is as follows:

P37 promoter: the nucleotides from No. 14 to No. 275 of SEQ ID No: 38;
the constitution of the FGF2 coding region: the nucleotides from No. 276 to No. 902 of SEQ ID No: 38;
the signal sequence: the nucleotides from No. 276 to No. 419 of SEQ ID No: 38;
the FGF2 sequence: the nucleotides from No. 420 to No. 881 of SEQ ID No: 38;
a histidine tag sequence: the nucleotides from No. 882 to No. 899 of SEQ ID No: 38;
a stop codon: the nucleotides from No. 900 to No. 902 of SEQ ID No: 38;
Hu terminator: the nucleotides from No. 903 to No. 1016 of SEQ ID No: 38;
The amino acid sequence encoded by said unit is expressed in SEQ ID No: 40, and its constitution is further indicated below.
the constitution of FGF2 coding region: the amino acids from No. 1 to No. 208 of SEQ ID No: 40;
the signal sequence: the amino acids from No. 1 to No. 48 of SEQ ID No: 40 (of which the amino acids from No. 1 to No. 37 corresponds the putative signal peptide region, the amino acids from No. 38 to No. 48 corresponds the putative spacer region, and the putative cleavage site appears between amino acids No. 37 and No. 38);
the FGF2 sequence: the amino acids from No. 49 to No. 202 of SEQ ID No: 40;
a histidine tag sequence: the amino acids from No. 203 to No. 208 of SEQ ID No: 40;

(4) Preparation of Recombinant *Bifidobacterium*.

Competent cells of the strains *Bifidobacterium longum* 105A and *Bifidobacterium breve* JCM1192 were produced according to the methods described in Rossi et al., Letters in Applied Microbiology (1997) 24: 33-36. Namely, said *Bifidobacterium* were cultured in IMR medium to early logarithmic growth phase, washed with PBS buffer, suspended in KMR buffer and rapidly frozen using liquid nitrogen to give the competent cells. These competent cells were thawed on ice, mixed with the above-mentioned plasmid pFGF12a or pBEshuttle (a mock vector described in International Publication No. WO 2011/093465; no FGF expression), and electroporated using the Gene Pulser II (Bio-Rad Laboratories, Inc.). The electroporation was carried out using a cuvette with 0.2 cm gap under the condition of at 2 kV, 25 μF and 200Ω. The transformed *Bifidobacterium* was spread onto an IMR agar medium (comprising 75 μg/mL spectinomycin) and cultured at 37° C. for 2 days under an anaerobic condition. Well isolated colonies formed on the agar medium were picked up to obtain the recombinant *Bifidobacterium*.

(5) Protein Expression Analysis (Western Blotting)

As a medium for culturing *Bifidobacterium*, 10 mL of MRS medium (oxide) was supplemented with 200 μL of Vitamin C/cystine solution (containing 350 mg/mL of ascorbic acid and 20 mg/mL of L-cystine) and 10 μL of 75 mg/mL of spectinomycin solution. Into this adjusted medium, the above-mentioned recombinant Bifidobacteria, i.e., *B. longum* 105A/pFGF12a and *B. longum* 105A/pBEshuttle were inoculated, and cultured at 37° C. for 24 hours under an anaerobic condition (an activated culture solution). The activated culture solution was inoculated into a medium which is prepared by adding to said adjusted medium sodium phosphate buffer at final concentration of 166 mM, and cultured at 37° C. for 18 hours under an anaerobic condition.

*Bifidobacterium breve* JCM1192/pFGF12a and *Bifidobacterium breve* JCM1192/pBEshuttle were also cultured in a similar manner as above, except using RCM medium instead of MRS medium. The Vitamin C/cystine solution was not added.

The culture supernatant of the recombinant *Bifidobacterium* described as above was treated with trichloroacetic acid (TCA) precipitation method according to conventional methods, then redissolved in 1×SDS sample buffer. It was then heated at 95° C. for 3 minutes and subjected to Western blot analysis.

Figure 17:
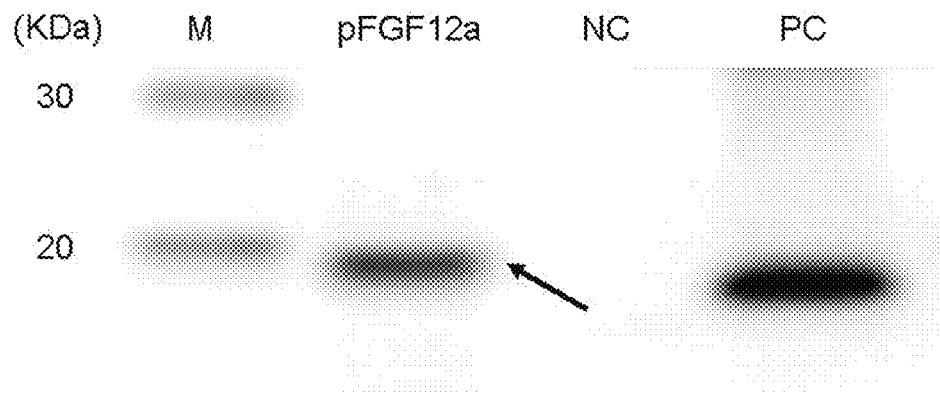
FIG. 17 shows the results of Western blotting using culture supernatant of *Bifidobacterium longum* 105A that has been transformed with pFGF12a. *Bifidobacterium longum* 105A transformed with pBEshuttle is used as a negative control, and hFGF2 is used as a positive control. A band of approximately 20 kDa was confirmed, being considered to be hFGF2.
Figure 18:
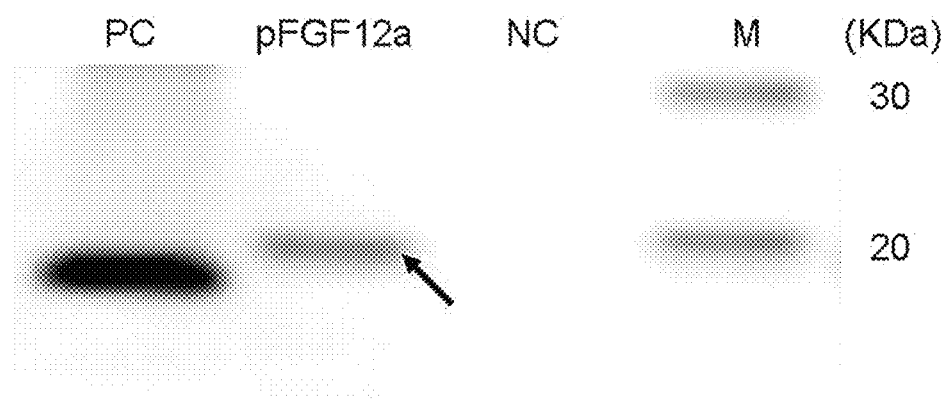
FIG. 18 shows the results of Western blotting using culture supernatant of *Bifidobacterium breve* JCM1192 that has been transformed with pFGF12a. *Bifidobacterium breve*

The sample described as above was electrophoresed using Mini-PROTEAN® TGX gel (4 to 20%, Bio-Rad) and 1×SDS buffer. An electrophoresis apparatus Mini PROTEAN® Tetra System (Bio-Rad) was used. After being electrophoresed, the gel was transferred onto an iBlot Transfer Stacks using the iBlot Gel Transfer Device. Transferred membrane was washed 3 times in TTBS for 5 minutes each, followed by blocking with 2% blocking solution (Block Ace). After adding a primary antibody Anti FGF-2 human rabbit poly (H-131, Santa Cruz Biotechnology Inc.), the membrane was shaken overnight at 4° C. After the reaction with the primary antibody, the membrane was repeatedly washed 6 times with TTBS for 5 minutes each. After adding a secondary antibody Goat anti-rabbit IgG HRP (Santa Cruz Biotechnology Inc.), the membrane was shaken at room temperature for 3.5 hours. This membrane was repeatedly washed 6 times with TTBS for 5 minutes each, followed by illumination using the illuminating reagent within the ECL Advance Western Blotting Detection Kit (GE Healthcare), detected by an imaging analyzer (Fluor-S MAX, Bio-Rad) (FIGS. 17 and 18).

(6) Protein Expression Analysis (ELISA)

The culture supernatant was prepared in a similar manner as above up to the step before TCA precipitation, then hFGF2 content was quantified using human FGF2 ELISA kit (Quantikine® ELISAHuman FGF basic Immunoassay, R&D systems, catalogue No: DFB50).

The hFGF2 content in the culture supernatant was 33,058 pg/mL for *B. longum* 105A/pFGF12a, whereas it was 0 pg/mL for the negative control *B. longum* 105A/pBEshuttle. On the other hand, it was 11,429 pg/mL for *Bifidobacterium breve* JCM1192/pFGF12a and 0 pg/mL for its negative control *Bifidobacterium breve* JCM1192/pBEshuttle.

Example 6: Evaluating In Vivo Therapeutic Effect in Ischemic Model Mouse

In order to examine the therapeutic effect of the gene transfer carrier of the invention at ischemic disease site, an ischemic model mouse was produced and administered the human FGF2 secretory *Bifidobacterium*.

(1) Preparation of Model.

As a test animal, 6- to 8-week-old female Balb/c mice (from CHARLES RIVER LABORATORIES JAPAN, INC.) were used, and the lower limb ischemia model mouse (ischemic model) was prepared using the following procedure. Animals were anesthetized by an intraperitoneal injection of 0.3 ml of 3.6% chloral hydrate (from Nacalai Tesque). After epilation of the area from abdomen to lower leg, the common femoral artery, deep femoral artery and superficial femoral artery were ligated with 8-0 polypropylene threads, and the superficial femoral artery was excised. After the interior of the wound was washed with physiological saline, the wound was sutured with a 5-0 nylon thread.

(2) Blood Flow Measurement Using a Laser Doppler Blood-Flowmeter.

After the mouse was anesthetized, blood flow was measured using a laser Doppler blood flow meter (Moor Instruments). The blood flow was quantified on both sides from lower leg to digit tip, expressed as an ischemic side/non-ischemic side ratio. The blood flow measurement was carried out immediately after producing the model, and at 3 to 4 days, 6 days and 8 days after producing the model.

(3) Administration of the Genetic Recombinant *B. Longum*

The human FGF2-secreting *Bifidobacterium* and control non-secreting *Bifidobacterium* were cultured for two passes in MRS medium (from KANTO KAGAKU CO., INC.). The culture solution was then washed by centrifugal washing with physiological saline, suspended in physiological saline and used. On the day after the production of the model, the cells were administered to the orbital sinus at the concentration of $1 \times 10^9$ cfu/ml in 0.2 ml, then blood flow in the lower limb was measured as mentioned above (2).

The results are displayed in FIGS. 19 and 20, and show the blood flow improving effects of the human FGF2-secreting *B. longum* and the human FGF2-secreting *B. breve*, respectively. In the group treated with the human FGF2-secreting *B. longum*, a significant improvement in blood flow was observed at Day 6 and thereafter as compared to the PBS-treated group (longum FGF12a vs PBS; at Day 6, 0.41±0.11 vs 0.14±0.02; at Day 8, 0.55±0.11 vs 0.32±0.08). In the group treated with the human FGF2-secreting *B. breve*, a significant improvement in blood flow was observed at Day 8 (breve FGF12a vs breve control, 0.67±0.11 vs 0.38±0.02). No significant difference was observed between groups treated with the non FGF-secreting bacterium (control) and with PBS.

INDUSTRIAL APPLICABILITY

In accordance with the gene transfer carrier of the present invention, a gene transfer carrier that colonizes and grows specifically at the site of an ischemic disease and disappears as the disease state improves can be provided. Therefore, compared with a conventional method, an angiogenic therapy can be carried out simply with low invasiveness. Furthermore, since the gene transfer carrier itself is formed from a bacterium, there is no problem with the efficiency with which the gene is transferred to a target site, and a treatment can be carried out with very high efficiency compared with the conventional art. This enables a target such as the elderly, for whom angiogenic therapy should naturally be effective but who cannot be treated because of problems such as high invasiveness and systemic side effects, to be treated effectively.

---

The invention claimed is:

1. A method for diagnosing or treating an ischemic disease, the method comprising administering an anaerobic bacterium that can specifically grow at the site of an ischemic disease and expresses at least one type of protein that is useful for the diagnosis or treatment of an ischemic disease, wherein the anaerobic bacterium is one that has been transformed using a transforming plasmid, wherein said transforming plasmid is a non-shuttle plasmid.

2. The method according to claim 1, wherein said administering is systemically administering.

3. The method for diagnosing or treating an ischemic disease according to claim 1, wherein said transforming plasmid comprises a DNA sequence coding for the at least one type of protein that is useful for the diagnosis or treatment of an ischemic disease.

4. The method for diagnosing or treating an ischemic disease according to claim 1, wherein the ischemic disease is a chronic ischemic disease.

5. The method for diagnosing or treating an ischemic disease according to claim 1, wherein the anaerobic bacterium is a nonpathogenic enterobacterium.

6. The method for diagnosing or treating an ischemic disease according to claim 1, wherein the anaerobic bacterium is a *Bifidobacterium*.

7. The method for diagnosing or treating an ischemic disease according to claim 6, wherein the *Bifidobacterium* is one type selected from the group consisting of *Bifidobacterium adolescentis*, *Bifidobacterium angulatum*, *Bifidobacterium animalis*, *Bifidobacterium asteroides*, *Bifidobacterium bifidum*, *Bifidobacterium boum*, *Bifidobacterium breve*, *Bifidobacterium catenulatum*, *Bifidobacterium choerinum*, *Bifidobacterium coryneforme*, *Bifidobacterium cuniculi*, *Bifidobacterium denticolens*, *Bifidobacterium dentium*, *Bifidobacterium gallicum*, *Bifidobacterium gallinarum*, *Bifidobacterium globosum*, *Bifidobacterium indicum*, *Bifidobacterium infantis*, *Bifidobacterium inopinatum*, *Bifidobacterium lactis*, *Bifidobacterium lactentis*, *Bifidobacterium liberorum*, *Bifidobacterium longum*, *Bifidobacterium magnum*, *Bifidobacterium merycicum*, *Bifidobacterium minimum*, *Bifidobacterium mongoliens*, *Bifidobacterium parvulorum*, *Bifidobacterium pseudocatenulatum*, *Bifidobacterium pseudolongum*, *Bifidobacterium psychraerophilum*, *Bifidobacterium pullorum*, *Bifidobacterium ruminale*, *Bifidobacterium ruminantium*, *Bifidobacterium saeculare*,

*Bifidobacterium scardovi, Bifidobacterium subtile, Bifidobacterium suis, Bifidobacterium thermacidophillum,* and *Bifidobacterium thermophilum.*

8. The method for diagnosing or treating an ischemic disease according to claim 7, wherein the *Bifidobacterium* is *Bifidobacterium longum*.

9. The method for diagnosing or treating an ischemic disease according to claim 1, wherein the at least one type of protein that is useful for the diagnosis of an ischemic disease is a fluorescent protein.

10. The method for diagnosing or treating an ischemic disease according to claim 1, wherein the at least one type of protein that is useful for the treatment of an ischemic disease is one type selected from the group consisting of fibroblast growth factor (FGF), endothelial cell growth factor (ECGF), vascular endothelium growth factor (VEGF), hepatocyte growth factor (HGF), angiogenic growth factor (AGF), platelet-derived growth factor (PDGF), transforming growth factor β(TGFβ), a protein having angiogenesis promoting activity, a factor involved in vasodilation, a colony stimulating factor, nerve growth factor (NGF), brain-derived neurotrophic factor (BDNF), a neurotrophin, and insulin-like growth factor (IGF).

11. The method for diagnosing or treating an ischemic disease according to claim 3, wherein the transforming plasmid further comprises a gene sequence coding for a secretory signal peptide.

12. The method for diagnosing or treating an ischemic disease according to claim 3, wherein the transforming plasmid comprises pTB6 rep unit.

13. The method for diagnosing or treating an ischemic disease according to claim 3, wherein the transforming plasmid has an expression cassette comprising p37 promoter, HU terminator and a gene coding for FGF2.

14. The method for diagnosing or treating an ischemic disease according to claim 3, wherein the transforming plasmid comprises a DNA sequence coding for a polypeptide having the sequence described in SEQ ID NO: 40.

15. The method for diagnosing or treating an ischemic disease according to claim 3, wherein the transforming plasmid is pFGF12a having the sequence described in SEQ ID NO: 38.

16. The method for diagnosing or treating an ischemic disease according to claim 10, wherein the protein having angiogenesis promoting activity is angiopoietin or ephrin.

17. The method for diagnosing or treating an ischemic disease according to claim 10, wherein the factor involved in vasodilation is a prostaglandin.

18. The method for diagnosing or treating an ischemic disease according to claim 10, wherein the colony stimulating factor is granulocyte colony stimulating factor (G-CSF) or granulocyte-macrophage colony stimulating factor (GM-CSF).

19. The method for diagnosing or treating an ischemic disease according to claim 10, wherein the neurotrophin is neurotrophin 3.

* * * * *